(12) United States Patent
Thoorens et al.

(10) Patent No.: US 8,329,221 B2
(45) Date of Patent: Dec. 11, 2012

(54) MICROCRYSTALLINE CELLULOSE AND CALCIUM PHOSPHATE COMPOSITIONS USEFUL AS PHARMACEUTICAL EXCIPIENTS

(75) Inventors: Gregory Thoorens, Ganshoren (BE); Bruno LeClercq, Brussels (BE); Thomas Ruszkay, Hockessin (DE)

(73) Assignee: FMC Corporation, Philadelphia, PA (US)

( * ) Notice: Subject to any disclaimer, the term of this patent is extended or adjusted under 35 U.S.C. 154(b) by 29 days.

(21) Appl. No.: 12/917,904

(22) Filed: Nov. 2, 2010

(65) Prior Publication Data

US 2011/0104288 A1 May 5, 2011

Related U.S. Application Data

(60) Provisional application No. 61/258,391, filed on Nov. 5, 2009.

(51) Int. Cl.
*A61K 9/14* (2006.01)
*A61K 47/02* (2006.01)

(52) U.S. Cl. ........................................ 424/489; 514/770

(58) Field of Classification Search .................. None
See application file for complete search history.

(56) References Cited

U.S. PATENT DOCUMENTS

| | | | |
|---|---|---|---|
| 4,744,987 A * | 5/1988 | Mehra et al. | 424/687 |
| 5,747,067 A | 5/1998 | Auguello | |
| 5,858,409 A | 1/1999 | Karetny | |
| 6,103,260 A | 8/2000 | Luber et al. | |
| 6,123,964 A | 9/2000 | Asgharnejad et al. | |
| 6,866,867 B2 * | 3/2005 | Staniforth et al. | 424/499 |
| 6,936,277 B2 | 8/2005 | Staniforth et al. | |
| 6,936,628 B2 | 8/2005 | Lee | |
| 2002/0176889 A1 | 11/2002 | Lemmens et al. | |
| 2003/0185891 A1 | 10/2003 | Crew et al. | |
| 2008/0213360 A1 | 9/2008 | Thoorens et al. | |
| 2009/0142398 A1 * | 6/2009 | Philip et al. | 424/484 |

FOREIGN PATENT DOCUMENTS

| | | |
|---|---|---|
| EP | 0124027 A1 | 11/1984 |
| EP | 1226818 | 7/2002 |
| WO | WO 8102521 A1 | 9/1981 |
| WO | WO 03/096963 A1 | 11/2003 |
| WO | WO 2005/030115 A1 | 4/2005 |
| WO | WO 2005/030116 A1 | 4/2005 |
| WO | WO 2005/030379 A1 | 4/2005 |
| WO | WO 2006/032828 A1 | 3/2006 |

OTHER PUBLICATIONS

Notification of Transmittal of the International Search Report and the Written Opinion of the International Searching Authority, or the Declaration, International Application No. PCT/US2010/055068, mailing date of Jul. 28, 2011.

Freitag, et al., "Coprocessing of Powdered Cellulose and Magnesium Carbonate: Direct Tableting Versus Tableting After Roll Compaction/Dry Granulation". Pharmaceutical Development and Technology, 10, pp. 353-362, (2005).

Kleinebudde P., "Roll Compaction/Dry Granulation: Pharmacuetical Applications", European Journal of Pharmaceutics and Biopharmaceutics 58, pp. 317-326, (2004).

Rowe, et al., Handbook of Pharmaceutical Excipients, Sixth Edition, "Milled Material (Anahydrous Dibasic Calcium Phosphate) is Typically use in Wet-granulated or Roller-compacted Formulations", (2009).

Budenheim, Di-Cafos PA, Used as "Dry and Wet Granulation Fillers" 3 pages, (May 2010).

* cited by examiner

*Primary Examiner* — Suzanne Ziska
(74) *Attorney, Agent, or Firm* — FMC Corporation

(57) ABSTRACT

Coprocessed compositions containing calcium phosphate and microcrystalline cellulose are useful as excipients in the preparation of solid dosage forms containing active pharmaceutical ingredients, particularly those prepared by processes involving multiple compaction steps. Such compositions may be obtained by preparing aqueous slurries of microcrystalline cellulose and calcium phosphate and drying such slurries to produce particulate products. The coprocessed products exhibit improved compactibility, as compared to dry physical blends of the same components.

20 Claims, 20 Drawing Sheets

MICROCRYSTALLINE CELLULOSE AND CALCIUM PHOSPHATE COMPOSITIONS USEFUL AS PHARMACEUTICAL EXCIPIENTS

FIELD OF THE INVENTION

This invention relates to particulate compositions useful as excipients in pharmaceutical formulations and granulates and solid dosage forms containing such excipients and active pharmaceutical ingredients.

DESCRIPTION OF THE RELATED ART

Discrete dosages of pharmaceutical compositions suitable for oral administration are conveniently administered as solid dosage forms, typically tablets. In addition to the therapeutic ingredient or ingredients (commonly referred to as "actives," "active pharmaceutical ingredients," or "APIs"), the tablet comprises pharmaceutically acceptable materials, known as excipients, that are not actives and do not provide a therapeutic effect, but are added to the tablet formulation to confer specific properties not related to the activity of the active.

There are three general methods of preparation of tablets: (1) direct compression; (2) dry granulation; and (3) wet granulation. In direct compression, the powdered material(s) to be included in the tablet (including the active and the excipients) are blended together and compressed directly without intermediate processing, such as granulation. Although direct compression is the most effective and favorable manufacturing process for the production of solid dosage forms, such as tablets, many tablet formulations cannot be processed using direct compression due to certain properties of the formulations such as poor flow or low bulk density. For example, poor flow properties may result in unacceptably high variances in drug dosages from tablet to tablet.

Granulation procedures may be used where poor flow or low bulk density of the direct compression mix precludes tabletting by direct compression. Granulation also improves content uniformity of the active, and reduces dust generation. Dry granulation includes mixing the ingredients (which may include the active as well as one or more excipients such as binders, fillers, disintegrants, or lubricants), roller compacting or slugging the mix, dry screening or milling to a coarse dry granulate and compressing the granules. The granules may be combined with one or more further excipients (binder, distintegrant, lubricant, etc.) prior to recompaction. The wet granulation procedure includes mixing some or all of the ingredients and thereafter adding water to the mixed powders (alternatively, one or more of the ingredients, particularly a binder, may be in suspension or solution when combined with the other ingredients). The resulting wet mass is screened, dried, optionally combined with one or more further excipients such as lubricant, binder, filler or disintegrant, and compressed into tablets.

In dry granulation, the tablet ingredients are not exposed to moisture, solvents and heat. Thus, dry granulation can be used to process moisture, solvent and/or heat sensitive actives. Dry granulation can be carried out by slugging or by roller compaction. Slugging is a double compression process. The material to be tabletted is compressed to a large compressed mass, or "slug," which is milled to a granulate, with the granulate then converted to tablets by a second compression process. Because slugging is a slow and uneconomic process, roller compaction has become the method of choice for dry granulation. Roller compaction has all the benefits of a granulation process, such as improved material flow behavior and content uniformity. In addition, roller compaction is high-volume and more economical to operate than wet granulation.

During the roller compaction process, at least a portion of the tablet formulation (the "granulate formulation") is compacted and densified by two counter-rotating high-pressure rollers, and the resulting material milled to uniform size. The resulting granulate may be subsequently tabletted with or without additional excipients to form tablets. The tablet is formed by pressure acting on the tablet formulation in a die on a tablet press. A tablet press includes a lower punch which fits into a die from the bottom and an upper punch having a corresponding shape and dimension, which enters the die cavity from the top after the tablet formulation fills the die cavity. The tablet is formed by pressure applied to the tablet formulation in the die by the lower and upper punches.

Because of its inherent compactibility characteristics, microcrystalline cellulose (MCC) finds widespread use as an excipient in pharmaceutical formulations. Good binding and disintegration properties are also obtained when MCC is used in tablet formulations.

Tablet formation by roller compaction followed by tabletting includes two compaction steps. However, after the first compaction step, the MCC granulate may have insufficient compactibility for the second compaction, i.e., tabletting, step. Therefore a need exists for microcrystalline cellulose-containing binders that can be used to prepare solid dosage forms by processes involving multiple compaction steps such as roller compaction and tabletting, or slugging. The binder must have sufficient compactibility for the second compaction step. Unfortunately, adequate recompactibility has proven to be challenging to achieve.

BRIEF SUMMARY OF THE INVENTION

The invention provides a coprocessed composition useful as a pharmaceutical excipient comprising particles of at least one calcium phosphate and particles of microcrystalline cellulose (the composition hereinafter sometimes being referred to as "the particulate product of the invention"). The term "coprocessed" as used in this specification refers to the physical processing of the calcium phosphate with microcrystalline cellulose in a manner that imparts improved physical characteristics to the coprocessed mixture, not exhibited by either microcrystalline cellulose or calcium phosphate alone or by simple blends or dry mixtures of microcrystalline cellulose and calcium phosphate. Such coprocessing may be accomplished, for example, by the mixing of the two components dispersed in an aqueous medium, followed by drying to recover the coprocessed composition.

In accordance with the present invention, a composition of matter useful as a pharmaceutical excipient is provided by particulate coprocessed microcrystalline cellulose and calcium phosphate, the two components in one embodiment being present in a weight ratio of from about 85:15 to about 55:45 microcrystalline cellulose:calcium phosphate. The microcrystalline cellulose and calcium phosphate are intimately associated in the particulate product of the invention and may be present as agglomerates of the two components. For example, at least a portion of the calcium phosphate particles may be embedded within the pores of the microcrystalline cellulose particles. The particulate product of the invention may be obtained by forming an aqueous slurry of the two components and then drying the slurry.

Microcrystalline cellulose and dibasic calcium phosphate have commonly been used as individual ingredients in the form of physical dry blends in dry granulation processes (i.e., slugging or roller compaction). However, it has now been unexpectedly discovered that a particulate product produced by an aqueous slurry coprocessing and co-drying process in accordance with the present invention exhibits synergistic performance as compared to analogous physical dry blends of the same components. Both compactibility (the production of slugs or ribbons on a compactor) and recompactibility (the production of tablets on a tabletting press using a granulate obtained from an initial compaction) are improved. That is, at a given compaction pressure, a ribbon or tablet produced using the particulate product of the invention has a higher tensile strength than an analogous ribbon or tablet produced using an excipient which is a physical dry blend of microcrystalline cellulose and calcium phosphate. Alternatively, to achieve a desired tensile strength in a ribbon or tablet, a lower compaction pressure is needed when the particulate product of the invention is used in place of an analogous dry physical blend of microcrystalline cellulose and calcium phosphate. The enhanced functionality of the particulate product of the invention provides strong roller-compacted ribbons or slugs, which enables satisfactory roller compaction of otherwise poorly compactible active pharmaceutical ingredients. The need to use extragranular excipients is reduced or avoided altogether due to the improved recompaction characteristics of the particulate product furnished by the present invention.

Thus, in one embodiment of the invention, granules are prepared by roller compacting a dry mixture comprising the particulate product of the invention and at least one active pharmaceutical ingredient (API), optionally also comprising at least one disintegrant and/or at least one lubricant and/or at least one filler, and grinding (milling) the resulting compacted ribbon to produce granules. The granules are then compacted to form tablets or other solid dosage forms. Alternatively, the granules may also be used as such (without being recompacted) in sachets or hard capsules, for example.

Additionally, a composition useful as a pharmaceutical excipient comprising dried particulate agglomerates is provided, wherein the agglomerates are obtained by forming a well-dispersed aqueous slurry of particulate microcrystalline cellulose and at least one particulate calcium phosphate and drying the aqueous slurry.

In another aspect, the invention provides a process for preparing a composition useful as a pharmaceutical excipient, comprising:
  a) forming a well-dispersed aqueous slurry of microcrystalline cellulose and at least one calcium phosphate; and
  b) drying the aqueous slurry by removing water therefrom to yield a particulate product.

In yet another aspect, a granulate or tablet formulation is provided which comprises at least one active (i.e., an API) and a particulate product obtained by a process comprising:
  a) forming a well-dispersed aqueous slurry of microcrystalline cellulose and at least one calcium phosphate; and
  b) drying the aqueous slurry by removing water therefrom to yield a particulate product.

Still another aspect of the invention provides a method for making a granulate, wherein the method comprises the steps of:
  a) applying pressure to a granulate formulation to form a compact; and
  b) milling the compact to form a granulate;
  wherein the granulate formulation comprises at least one active (i.e., an API) and a particulate product obtained by a process comprising:
  a) forming a well-dispersed aqueous slurry of microcrystalline cellulose and at least one calcium phosphate; and
  b) drying the aqueous slurry by removing water therefrom to yield a particulate product.

The granulate thus obtained may be recompacted to provide a solid dosage form such as a tablet.

Further provided by the invention is a solid dosage form comprising a particulate product, at least one active, and, optionally, at least one additional excipient (e.g., a filler, binder, lubricant, disintegrant, and/or glidant) in the form of a compacted tablet, wherein the particulate product is obtained by a process comprising:
  a) forming a well-dispersed aqueous slurry of particulate microcrystalline cellulose and at least one calcium phosphate; and
  b) drying the aqueous slurry by removing water therefrom.

The particulate product of the invention can provide one or more of the following benefits or advantages when utilized as a pharmaceutical excipient. The need to use multiple different excipients or to introduce portions of the same excipient at different points in a granulation/tabletting process may be reduced or eliminated altogether, thereby simplifying such processes, lowering manufacturing costs, and/or improving quality control. A compacted material prepared using the particulate product of the invention can exhibit a decreased tendency to generate fines when milled and screened into a granulate; this can minimize waste and/or avoid the need to recycle particles that are too small to be utilized in a subsequent tabletting step. Similarly, tablets containing the particulate product of the invention can have reduced friability as compared to tablets prepared using other binders (e.g., physical blends of microcrystalline cellulose and calcium phosphate particles). The tablets thus can display enhanced resistance to physical handling, helping to ensure that such tablets are intact and undamaged when they reach the consumer. Also, since a tabletting formulation containing the particulate product of the invention can use a lower compaction pressure to achieve a desired tensile strength, less wear on the tabletting equipment can be realized. In addition, improved yields can be obtained, as fewer tablets will fail to meet the minimum tensile strength requirements.

Figure 1:
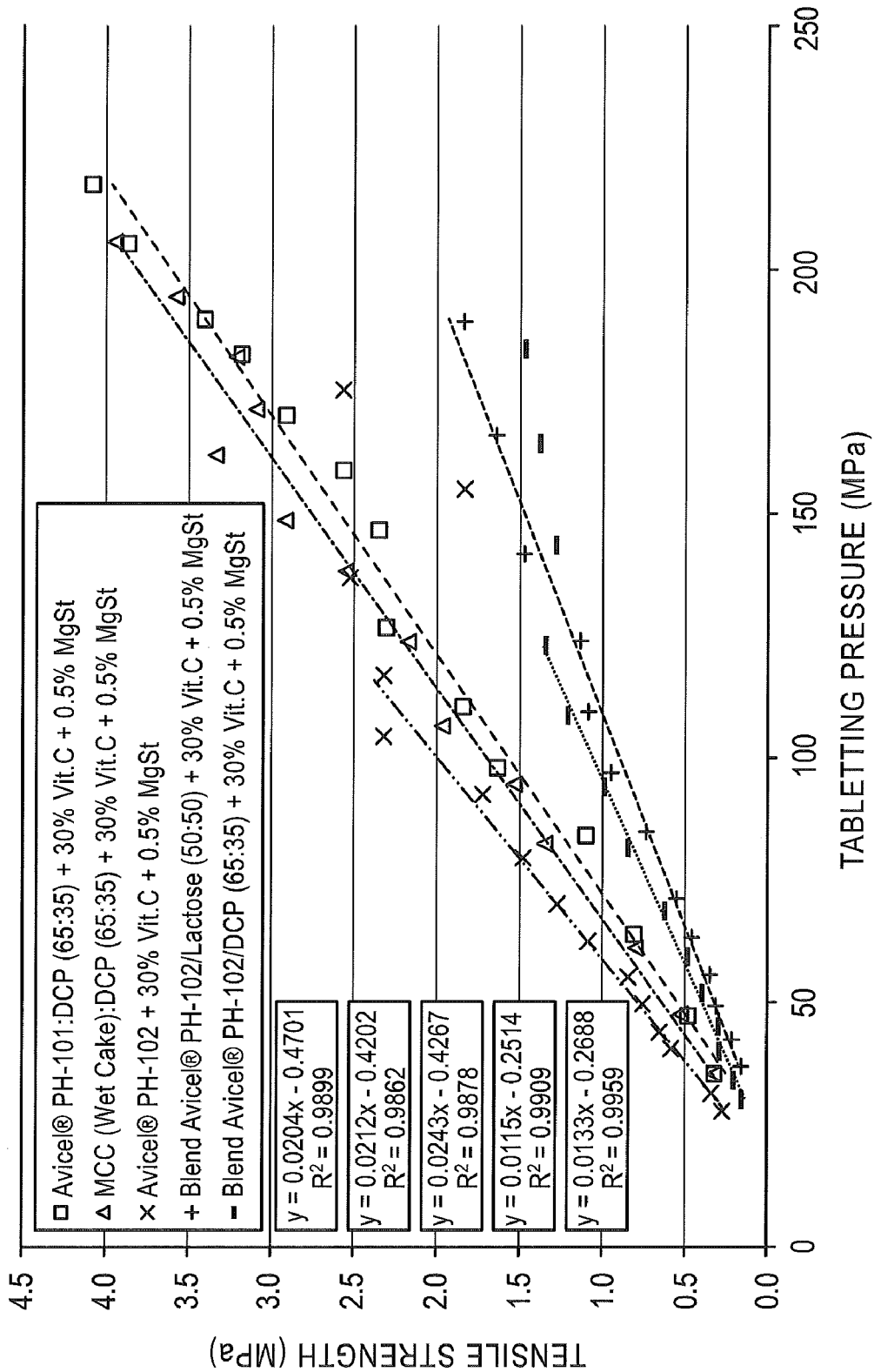
FIG. 1 is a graph comparing the compactibility of formulations containing Vitamin C, magnesium stearate and various excipients.

All the figures are described in more detail in the Examples section.

DETAILED DESCRIPTION OF CERTAIN EMBODIMENTS OF THE INVENTION

The particulate product of the invention is preferably a spray dried material. The particle size of the particulate product should be such that substantially all the particles have a particle size less than a No. 60 sieve (250 μm) and preferably have a median particle size in the range of from 20 μm to 150 μm.

The particulate product may advantageously be prepared by forming a well-dispersed aqueous slurry of microcrystalline cellulose and calcium phosphate, both being present in particulate form. The amounts of each component are, in one aspect of the invention, selected to provide a component ratio in the range of from 85:15 to 55:45 (on a weight basis) microcrystalline cellulose:calcium phosphate for the particulate product. The aqueous slurry is dried by removing water therefrom, to yield the particulate product of the invention.

The aqueous well-dispersed slurry of the two components is preferably formed by introducing microcrystalline cellulose and calcium phosphate into an aqueous medium in amounts that yield a relatively concentrated slurry of at least 10 wt % but no more than 40 wt % solids. The order of addition of the components is not believed to be particularly critical. Preferably, the slurry remains liquid (non-pasty), free-flowing, and relatively low in viscosity. In various embodiments of the invention, the viscosity of the slurry is not greater than about 40,000 cps, not greater than about 10,000 cps, or not greater than about 5000 cps. The aqueous slurry is preferably dried by spray drying to yield the particulate product.

The particulate product of this invention contains two essential components, microcrystalline cellulose and calcium phosphate. The two components are preferably are present in the product in a weight ratio in the range of about 90:10 to about 50:50, or about 85:15 to about 55:45, or about 80:20 to about 60:40 microcrystalline cellulose:calcium phosphate, although other ratios may also provide satisfactory performance depending upon the particular choice of components, particle size, and so forth.

In one aspect of the invention, microcrystalline cellulose and calcium phosphate are the only constituents of the particulate product. However, one or more other ingredients may also be incorporated into the particulate product during its preparation. These are ordinarily present in relatively small amounts, representing less than 30%, and preferably less than 20%, of the total particulate product weight. Such additives may be incorporated to facilitate the coprocessing procedure, particularly during the drying step, or to provide enhanced properties for the particulate product in its use as a pharmaceutical excipient. Examples of additives in these categories are binders, e.g., water-soluble gums like hydroxypropylmethylcellulose, methylcellulose, polyvinylpyrrolidone, etc.; lubricants, e.g., long chain fatty acid esters or salts thereof like palmitic and stearic acids; and disintegrants like cross-linked carboxymethylcellulose, starch, etc. In one embodiment of the invention, the particulate product is comprised from about 5 to about 15% by weight of a water-soluble binder such as methylcellulose.

The particulate product of this invention possesses desirable performance attributes that are not shown with the corresponding dry-blend of microcrystalline cellulose particles and calcium phosphate particles. The mechanism that occurs during the coprocessing procedure in accordance with this invention is not fully understood but appears to yield a particulate product in which the two essential components are in intimate association with each other. This intimate association or admixture of microcrystalline cellulose and calcium phosphate cannot be achieved through simple dry blending of these materials or even wet blending as a paste.

This intimate association of the two components manifests itself in the appearance of agglomerated particles, containing both microcrystalline cellulose and calcium phosphate, that result after drying of the slurry. It is believed that at least a portion of the calcium phosphate particles may be embedded within the pores of the microcrystalline cellulose particles. Generally speaking, it will be desirable for the median particle size of the microcrystalline cellulose to be greater than the median particle size of the calcium phosphate. For example, in certain embodiments the median particle size of the microcrystalline cellulose will be at least two, three, four or five times greater than the median particle size of the calcium phosphate.

Various characteristics of the particulate product, e.g., its particle size, moisture content, bulk density, will be described in detail below, in the context of the process by which this particulate product may be prepared. These physical characteristics are in large measure dependent on the manner in which the microcrystalline cellulose and calcium phosphate are coprocessed. It is for this reason that the conditions employed in the drying step in the coprocessing procedure are generally considered significant, and it is the reason that spray-drying is the preferred method for accomplishing the drying step.

In simple terms, a process for preparing the particulate product of this invention involves forming a well-dispersed aqueous slurry of microcrystalline cellulose and calcium phosphate, in which both materials are present as particulate solids. The relative amounts of the two components are adjusted in the slurry to yield the specific weight ratio desired in the recovered coprocessed product. Since the weight ratio of the two components in the particulate product corresponds closely to that in the precursor well-dispersed slurry, this ratio adjustment is relatively straightforward.

The process next involves drying the aqueous slurry by removing water from it to yield the particulate product. As mentioned earlier, spray drying is the preferred drying means but other drying methods, e.g., flash drying, fluidized bed drying, ring drying, micron drying, tray drying, vacuum drying, oven drying, radio frequency drying and microwave drying, may also be adapted for use in this coprocessing step.

The two components employed in forming the well-dispersed aqueous slurry are microcrystalline cellulose and calcium phosphate, although one or more additional components may also be utilized if so desired. The source and nature of these components are not considered critical. In one embodiment, the microcrystalline cellulose is wet cake from a conventional microcrystalline cellulose manufacturing process. The wet cake is material which has not yet been dried, sometimes termed "never dried" or hydrocellulose. The microcrystalline cellulose source may also be a conventional product which has already been dried.

The particle size of the microcrystalline cellulose used in the aqueous slurry is ordinarily that which is encountered in conventional microcrystalline cellulose product, or in its precursor wet cake, i.e., never dried product. The particle size is desirably such that substantially all particles are less than No. 60 sieve (250 μm) in size. In one embodiment, the microcrystalline cellulose has a median particle size of from about 20 μm to about 250 μm.

Specific size requirements for fine particle sizes, if desired, can be met through screening off unwanted coarse material or through conventional wet or dry attrition procedures. Such attrition may also be accomplished with the microcrystalline cellulose in the aqueous slurry. These size reduction procedures are ordinarily not required with microcrystalline cellulose as is now commercially produced.

The calcium phosphate employed in the present invention may be any of the various calcium salts of phosphorus-containing acids (e.g., phosphoric acid) known in the art, particularly the pharmaceutical excipient art. Monobasic, dibasic, and tribasic calcium phosphates in anhydrous or hydrated form may be utilized. Anhydrous as well as hydrated dibasic calcium phosphates (e.g., dibasic calcium phosphate dihydrate and anhydrous dibasic calcium phosphate) are especially preferred. Dibasic calcium phosphate is sometimes also referred to as dicalcium phosphate, calcium monohydrogen phosphate, dicalcium orthophosphate, or secondary calcium phosphate. The use of U.S.P. or Ph.Eur. grades of calcium phosphates is also preferred. For example, the dibasic calcium phosphates sold under the brand name EMCOMPRESS® by JRS Pharma GmbH & Co. KG and under the brand name Di-Cafos® by Budenheim are suitable for use in the present invention.

Calcium phosphate sizing is preferably such that substantially all particles are less than 200 μm in size and, more preferably, less than 50 μm. The median particle size of the calcium phosphate is desirably less than 100 μm and, more preferably, is less than 50 μm or less than 20 μm. In one embodiment, the median particle size of the calcium phosphate is about 5 to about 10 μm, e.g., about 7 μm.

Both microcrystalline cellulose and calcium phosphate, it should be recognized, are substantially insoluble in water. Consequently, the particle size of the material present in the well-dispersed aqueous slurry is directly related to the sizing of the two components introduced to the slurry; i.e., there is no appreciable dissolution of either of the two components in the aqueous slurry (although some attrition of the microcrystalline cellulose particles may take place).

The aqueous slurry of these two components may be prepared in any of several ways. The two solid components may both be introduced into a single aqueous medium, or each may be introduced separately into separate aqueous media which are then combined, or other analogous procedures may be devised.

One procedure involves dispersing the microcrystalline cellulose alone into an aqueous solution, preferably water. Typical solids concentrations for this aqueous mixture are from 5-25 wt % microcrystalline cellulose but 10-20 wt % microcrystalline cellulose is preferred.

Once the microcrystalline cellulose is well-dispersed in the aqueous slurry, the appropriate amount of calcium phosphate can then be added, in dry form, with mixing being continued during its addition. The exact amount of calcium phosphate to be added depends on the microcrystalline cellulose content of the slurry and the ratio of the two components desired in the coprocessed product. Water may also be added if a more dilute slurry is desired, but this is usually not required. If so desired, the pH of the slurry may be adjusted by the addition of one or more pH adjusting agents such as an acid or a base. Typically, the aqueous slurry has a pH within the range of about 3 to about 9.

The aqueous slurry containing the two components should be well mixed to assure uniform dispersion of the components throughout the aqueous medium. This is necessary to provide for a uniform, consistent component ratio in the particulate product, prepared via drying the aqueous slurry.

The total solids content of the aqueous slurry is preferably at least 10 wt %), based on the total slurry weight, and is more preferably at least 20 wt %) solids. The higher solids content levels are desirable since the amount of water that must be removed during the drying step is accordingly reduced. However, the solids content should preferably be kept below the level at which the slurry no longer is liquid and capable of being readily stirred.

The upper limit on solids content in the aqueous slurry is also typically determined by the operating constraints of the drying apparatus used. With the preferred spray drying procedure, solids contents of 20-30 wt % are representative for aqueous slurries that can be readily processed.

The temperature of the aqueous slurry is not critical. Ambient temperatures, of from about 10 to about 25° C., are preferred. Higher slurry temperatures may be employed, and these may be desirable with certain types of drying equipment.

The drying of the well-dispersed aqueous slurry is preferably accomplished by spray drying of the slurry. Conventional spray drying equipment may be employed, and operating procedures that are familiar to those experienced in the spray drying art are applicable to the spray drying step of this process. Drier (drier gas) outlet temperature is ordinarily used to control the residual moisture level obtained in the coprocessed particulate product.

Moisture levels of not more than about 5 wt % $H_2O$ are generally desired in the particulate, dried product, although, of course, the water content may be higher than 5 wt % and may be readily controlled by varying the drying conditions.

In the (preferred) spray-drying process, the aqueous slurry of microcrystalline cellulose and calcium phosphate may be atomized into droplets and brought together with a sufficient volume of hot air to produce evaporation and drying of the droplets. The dispersed slurry of microcrystalline cellulose and calcium phosphate preferably is pumpable and capable of being atomized. It is sprayed into a current of warm filtered air, which supplies the heat for evaporation and conveys a dried product to a collecting device. The air is then exhausted with the removed moisture. In one embodiment of the invention, the resultant spray-dried powder particles are approximately spherical in shape and are relatively uniform in size, thereby possessing good flowability. The coprocessed product comprises microcrystalline cellulose and calcium phosphate particles in intimate association with each other.

In a spray drying procedure, drier outlet temperatures are ordinarily in the range of about 40 to about 100° C. Corresponding drier inlet temperatures are higher, ordinarily in the range of about 90 to about 300° C.

The coprocessed product recovered from the drying operation is a free-flowing particulate solid, that is typically a granular white powder in appearance. The particle size of the product is a function of the particle sizing of the microcrystalline cellulose and calcium phosphate in the aqueous slurry and of the drying conditions employed for removing water from the slurry. Particle size may be influenced by spray dryer operating conditions, for example, such as droplet size, temperature, production rate, % slurry solids, type of atomizer, atomizer speed, air flow and chamber size. Furthermore, it is within the scope of the invention to sort or mechanically alter the dried coprocessed product so as to vary or select the particle size and particle size distribution as may be desired.

The particulate product in one embodiment of the invention has a particle size such that substantially all the particles have a size smaller than a No. 60 sieve (250 µm). Median particle size of the particulate material is, in one embodiment, in the range of from about 20 µm to about 200 µm, and in another embodiment is in the range of from about 30 µm to about 50 µm. "Median particle size," as used herein, refers to the D50 value as measured by laser diffraction using a Malvern Mastersizer 2000. The median particle size of the various particulate materials described herein may also be determined by laser diffraction using a Malvern Mastersizer 2000. The loose bulk density of the particulate product is typically less than 0.60 g/cc and greater than 0.20 g/cc. The pH of the particulate product is generally about 3 to about 12 or, in another embodiment about 5 to about 8.

The particulate product of the present invention is particularly useful as an excipient or binder in processes involving roller compaction, granulation, and/or tabletting.

For example, the particulate product may be utilized in the following process:
1) The particulate product is blended with an API, a filler, and a disintegrant;
2) The blend from step 1 is further blended with a lubricant, if needed to reduce sticking on the compaction rolls;
3) The blend is compacted, using a roller compactor;
4) The ribbon obtained by roller compaction is granulated and/or milled;
5) The granulate obtained from step 4 is screened (to control and/or modify the particle size of the granulate, as needed or desired);
6) The screened granulate is recompacted to form tablets.

If needed to improve stability or to modify the disintegration time and dissolution rate or profile of the tablets, extragranular disintegrant and/or lubricant may be blended with the screened granulate prior to step 6. However, in at least some embodiments of the invention, the productivity (operating cost) of the dry granulation process is improved by avoiding such additional steps, which are generally considered necessary in traditional roller compaction processes which utilize binders and fillers other than the particulate product described herein.

Roller compaction (also known in the art as "roll compaction") is a dry compaction/granulation process for tablet formation, which is used when a tablet formulation does not have the flow characteristics or high enough bulk density necessary for tablet formation. A roller compactor uses pressure to compact and densify the tablet formulation and to bind powders into granules. Actives that have been processed by roller compaction include, for example, acetylsalicylic acid (aspirin), acetaminophen, amoxicillin, ibuprofen, penicillin, ranitidine, and streptomycin.

Figure 3:
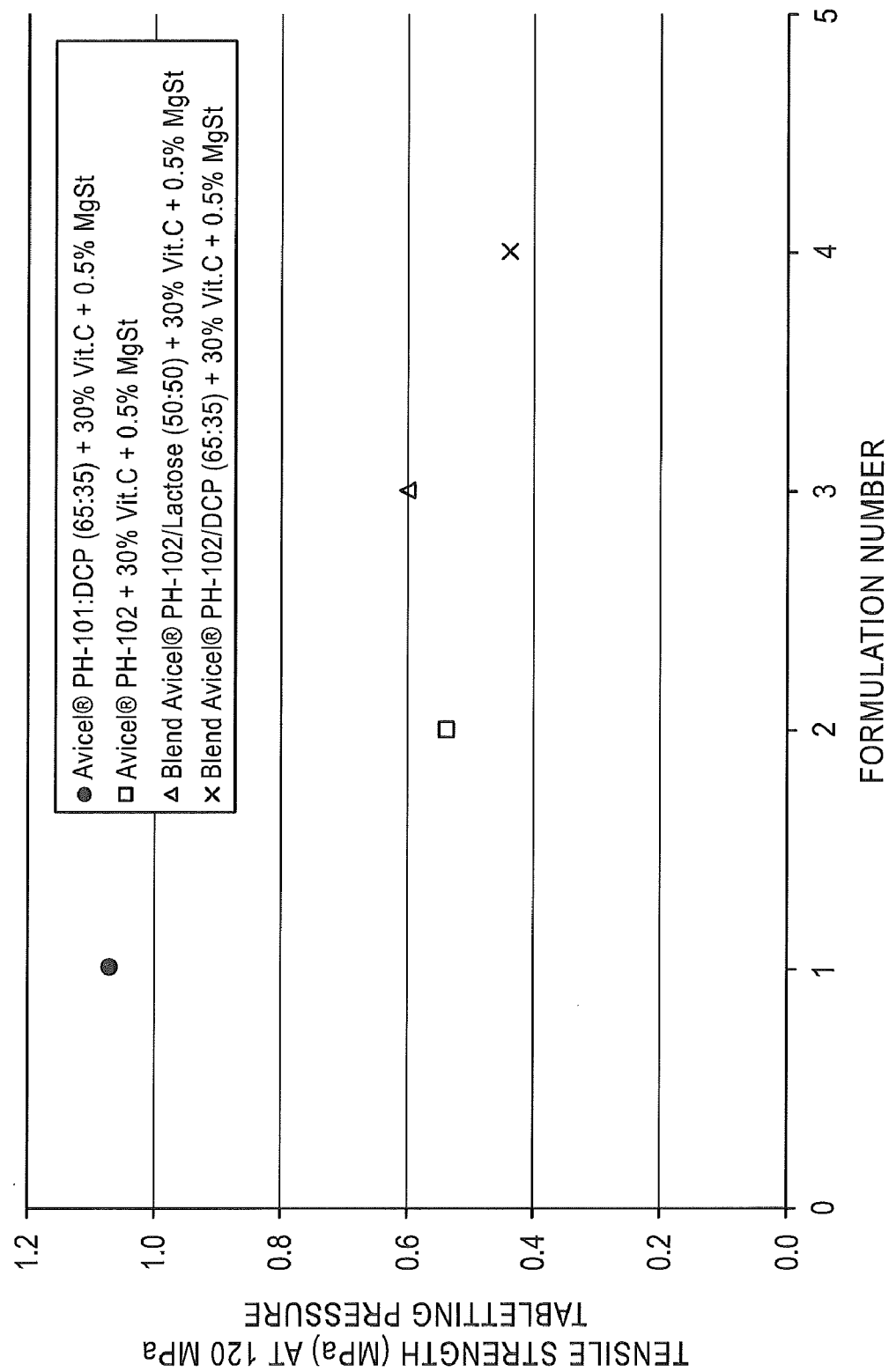
FIG. 3 is a chart comparing the recompactibility of formulations containing Vitamin C, magnesium stearate and various excipients at a given tabletting pressure.

The coprocessed particulate product of the present invention is especially suitable for use in connection with a granulation process. Granulation is a process of size enlargement in which small particles are gathered together into larger aggregates in which the original particles can still be identified. Uniformly mixed powders (granulate formulations) are compressed between counter rotating rollers to form a ribbon of compacted material that is then milled into granules. Thus, the coprocessed particulate product may be used as an ingredient in a granulate formulation which is then converted into a granulate. A schematic representation of a roller compactor is shown in FIG. 3 of U.S. Patent Publication No. 2008/0213360, incorporated herein by reference in its entirety for all purposes. A roller compactor comprises a roller assembly, press frame, hydraulic pressure system, and a feed system. The feed system is located immediately before the rollers and determines the rate of flow of the granulate formulation to the rollers. The feed system may comprise one or more feed screws that force the granulate formulation between the compacting rollers. The granulate formulation is compacted as it passes through the two compacting rollers. The volume of the granulate formulation decreases as it passes through the region of maximum pressure, where it is formed into a solid compacted material known as a sheet or ribbon. Compaction pressure is provided by the hydraulic pressure system, which can be adjusted to produce the desired compaction pressure. The hydraulic pressure system acts on one of the rollers. As shown in FIG. 3 of U.S. Patent Publication No. 2008/0213360, the roller compaction process may be a continuous process of compacting, milling, screening, and recycling the too-large granules ("Overs") and too small granules ("Fines") back to the process. One advantage of the present invention is the reduction in the amount of Fines produced during such a process when the particulate product of the invention is employed as an excipient.

Various configurations for the rollers are well known in the art and are described, for example, in A. M. Falzone, Ph.D. Thesis, Purdue University, 1990 (U.M.I., Ann Arbor, Mich., Order Number 9313940). Roller compaction equipment is commercially available from the Fitzpatrick Company, Elmhurst Ill. USA as CHILSONATOR® roll compactors. This equipment is described in "Introduction to Roll Compaction and the Fitzpatrick CHILSONATOR," published by The Fitzpatrick Company Europe.

The particulate product of the present invention is also suitable for use as a component of a tablet, which may for example be prepared directly from a physical dry blend of the particulate product in combination with one or more additional ingredients such as an API or from a granulate prepared as previously described herein (also possibly in combination with one or more additional ingredients). Tabletting is well known to those skilled in the art of tablet formation. The tablet is formed by pressure being applied to the tablet formulation on a tablet press. A tablet press includes a lower punch which fits into a die from the bottom and an upper punch having a corresponding shape and dimension, which enters the die cavity from the top after the tablet formulation fills the die cavity. The tablet is formed by pressure applied to the tablet formulation in the die by the lower and upper punches. The ability of the tablet formulation to flow freely into the die is important in order to ensure that there is a uniform filling of the die with continuous flow of tablet formulation from hopper to die. A lubricant, such as magnesium stearate, may be added to facilitate ejection of the tablet from the die following compaction, and to avoid sticking to the punch faces. Tabletting is well described in pharmaceutics textbooks such as AGENNARO, Remington: The Science and Practice of Pharmacy, 20th Ed., Lippincott Williams & Wilkins, Baltimore, Md., 2000.

In one aspect, the present invention provides a solid dosage form such as a tablet comprising the particulate product of the invention, one or more actives, and, optionally, one or more one or more pharmaceutically acceptable excipients. Such tablets may be prepared from a tablet formulation by combining the active or actives with at least one excipient according to conventional pharmaceutical compounding techniques. To prepare a solid dosage form, or tablet, by direct compaction, the tablet formulation must have the necessary physical characteristics. Among other things, the tablet formulation must be free flowing, must be lubricated, and, importantly, must possess sufficient compactibility to ensure that the solid dosage form remains intact after compaction, and is robust enough for subsequent operations, such as handling, coating, and packaging. The particulate product of the present invention has been found to impart unexpectedly improved properties to tablet formulations, particularly with respect to compactibility and recompactibility.

The tablet may be formed by pressure being applied to the tablet formulation on a tablet press. A tablet press includes a lower punch that fits into a die from the bottom and an upper punch having a corresponding shape and dimension that enters the die cavity from the top after the tablet formulation fills the die cavity. The tablet is formed by pressure applied on the lower and upper punches. The ability of the tablet formulation to flow freely into the die is important in order to ensure that there is a uniform filling of the die and a continuous movement of the material from the source of the tablet formulation, e.g., a feeder hopper. The lubricity of the tablet formulation is crucial in the preparation of the solid dosage forms because the compressed material must be readily released from the punch faces. The tablet must also eject cleanly from the die following compression.

Because actives do not always have these properties, methods of tablet formulation have been developed in order to impart these desirable characteristics to the tablet formulation. Typically, the tablet formulation comprises one or more additives, or excipients, that impart the desired free flowing, lubrication, and binding properties to the tablet formulation.

The excipients for dry granulate formulations should have good recompactibility and dilution potential to allow compaction of the granules into a tablet. The excipients should not accelerate chemical and/or physical degradation of the active and should not interfere with its biological availability. The excipients should be physiologically inert and should not unintentionally interfere with the tablet disintegration or dissolution of the active. They should show low lubricant sensitivity and ensure acceptable active content uniformity. Typical excipients are selected from the group consisting of binders, disintegrants, glidants, fillers, diluents, colorants, flavorants, stabilizers, and lubricants. The choice of the excipients and the composition of the tablet formulation depend on the active, the amount of active in the formulation, the type of tablet, the desired characteristics for both the tablet formulation and the resulting tablet, and the manufacturing process used. These include prompt release, for which the drug dissolves in a very short time, immediate release and modified release, which include most of the orally administered tablets that are swallowed.

Pharmaceutically acceptable excipients are well known to those skilled in the art and are disclosed for example, in Staniforth, U.S. Pat. No. 6,936,277, and Lee, U.S. Pat. No. 6,936,628, each of which is incorporated herein by reference in its entirety for all purposes. Microcrystalline cellulose is added to improve the compactibility of the tablets. Excipients such as diluents, binders, glidants, and lubricants are added as processing aids to make the tabletting operation more effective. Still other types of excipients enhance or retard the rate of disintegration of the tablet, improve the taste of the tablet, (for example, sweetening agents), or impart a color or flavor to the tablets.

One or more lubricants may be added to a tablet formulation comprising the particulate product of the present invention to prevent the formulation from sticking to the punches during tablet manufacture. Suitable lubricants include, for example, fatty acids, fatty acid salts, and fatty acid esters such as magnesium stearate, calcium stearate, stearic acid, sodium stearyl fumarate, hydrogenated vegetable oil and the like. Lubricants may typically comprise about 0.1 wt % to about 3.0 wt % or about 0.5 wt % to about 1 wt % of the formulation. Antiadherents may be utilized to prevent sticking of the tablet formulation to the punch face and die wall. They are used in combination with magnesium stearate when sticking is a problem. Commonly used antiadherents are cornstarch and talc. Diluents, fillers, or bulking agents in addition to the particulate product of the present invention may be added in order to increase the bulk weight of the material to be tabletted in order to make the tablet a practical size. This is often necessary where the dose of the active is relatively small. Suitable fillers for this purpose include, but are not limited to, lactose, dibasic calcium phosphate, calcium phosphate, powdered cellulose, dextrates, isomalt, calcium carbonate, magnesium carbonate, starch, pre-gelatinized starch, and mixtures thereof. Sugar alcohols such as sorbitol, mannitol and xylitol may also be used as fillers, especially in chewable tablet formulations. The most significant differences between sorbitol and mannitol are hygroscopicity and solubility. Sorbitol is hygroscopic above 65% relative humidity and mannitol is nonhygroscopic. The aqueous solubility of sorbitol is higher than mannitol.

One or more binders in addition to the particulate product of the present invention may be added to further modify the cohesive qualities of the powdered material(s). Suitable additional binders include starch, microcrystalline cellulose, and sugars such as sucrose, glucose, dextrose, and lactose. One or more stabilizers may be included in the tablet formulation to reduce the rate at which the active decomposes. Suitable stabilizers include antioxidants such as ascorbic acid. Additionally, one or more disintegrants may also be included in the tablet formulation to ensure that the tablet has an acceptable dissolution rate in an environment of use (such as the gastrointestinal tract). The disintegrant breaks up the tablets and the granules into particles of active and excipients. Superdisintegrants such as croscarmellose sodium, sodium starch glycolate, or crospovidone may also be employed.

One or more glidants may be used in the tablet formulation to improve flow. Because of the shape and size of the particles, glidants improve flow in low concentrations. They may be mixed in the final tablet formulation in dry form. Suitable glidants include, for example, alkali metal stearates, colloidal silicon dioxide (including materials sold under the brand names CAB-O-SIL®, SYLOID®, and AEROSIL®), and talc.

Desirable characteristics may be imparted to the tablet by colorants (i.e., dyes and pigments), natural or artificial sweeteners, and flavorants. Wetting agents, also called surface active agents or surfactants, may also be present. The tablet may also be coated.

Surfactants such as polysorbates, sodium lauryl sulphate, polyethylene glycol fatty acid esters, or polyethylene glycol ester salts may also be present in the formulation. To modify the release profile of the API, one or more matrix formers such as HPMC, carrageenan or alginate may optionally be included.

Tablets in accordance with the present invention may be any desired shape and size. For example, the size of round tablets may be about 50 mg to 500 mg and capsule-shaped tablets may be about 200 mg to 1200 mg in size. However, other formulations prepared in accordance with the invention may be suitably sized and shaped for other uses or locations, such as other body cavities, e.g., periodontal pockets, surgical wounds, and vaginally. For certain uses, such as chewable tablets, antacid tablets, vaginal tablets, and implants, the tablet may be larger.

The compositions are also suitable for use in enrobing processes to prepare solid dose forms. For example, solid dose forms may be prepared by lightly compacting a tablet formulation or granulate formulation in accordance with the present invention to form a powder compact and enrobing the powder compact with a film. The methods and apparatus for forming enrobed solid dose forms disclosed in WO 03/096963, WO 2005/030115, WO 2005/030116, WO 2005/030379, and WO 2006/032828, the disclosures of which are all incorporated herein by reference in their entirety for all purposes, may for example be adapted for use with solid dose forms prepared using the particulate products of the present invention.

The MCC/calcium phosphate-containing materials of the invention may be used as binders in solid dosage forms, such as tablets, that comprise one or more actives, and optionally, one or more other excipients. They are particularly useful as binders for formulations prepared by direct compression or processes involving compaction, granulation and recompaction. Although primarily useful in pharmaceutical and veterinary applications, they may be used in other areas, such as agriculture, food, cosmetics, and other industrial applications.

EXAMPLES

| Glossary | |
|---|---|
| Anhydrous EMCOMPRESS ® | dibasic calcium phosphate anhydrous, DC grade (JRS Pharma, Germany) |
| AVICEL ® HFE-102 | 100 μm coprocessed MCC/mannitol (FMC, Philadelphia) |

-continued

| Glossary | |
|---|---|
| AVICEL ® PH-105 | 20 μm microcrystalline cellulose (FMC, Philadelphia PA) |
| AVICEL ® PH-101 | 50 μm microcrystalline cellulose (FMC, Philadelphia PA) |
| AVICEL ® PH-102 | 100 μm microcrystalline cellulose (FMC, Philadelphia PA) |
| AVICEL ® PH-200 | 200 μm microcrystalline cellulose (FMC, Philadelphia PA) |
| Di-Cafos ® C92-04 | dibasic calcium phosphate anhydrous fine, 7 μm (Budenheim, Germany) |
| Di-Cafos ® C92-05 | dibasic calcium phosphate anhydrous, 7 μm (Budenheim, Germany) |
| Di-Cafos ® C92-12 | dibasic calcium phosphate anhydrous coarse, 80 μm (Budenheim, Germany) |
| Di-Cafos ® C92-01 | dibasic calcium phosphate dihydrate, 14 μm (Budenheim, Germany) |
| EMCOMPRESS ® Premium | dibasic calcium phosphate dihydrate, DC grade (JRS Pharma, Germany) |
| SuperTab ® 11SD | lactose monohydrate, DC grade (DMV Fonterra) |
| SuperTab ® 21AN | lactose anhydrous, DC grade (DMV Fonterra) |
| magnesium stearate | Vegetable 2257 (Tyco Mallinckrodt, St Louis MO USA) |
| MicroceLac ® 100 | coprocessed MCC/lactose (25:75 by weight) (Meggle Pharma, Waterburg Germany) |
| Vitamin C | ascorbic acid (crystalline) (Jiangsu Jiangshan Pharmaceutical Co., Ltd) |

Unless otherwise stated, all percentages or proportions provided herein are stated as percentages or proportions based on weight.

Preparation and Methods

Roller-compacted ribbons and granulates were prepared and tested as follows: Formulations containing 30 wt % Vitamin C were prepared by making a preblend of 6.95 kg of binder excipient(s) with 3 kg of Vitamin C as a model drug and blending for 10 minutes in a Pharmatech 50 Litre V Container rotating at 28 rotations per minute. Then 50 grams of magnesium stearate was added as a lubricant to the preblend and mixed for 2 minutes at 28 rpm. The blend, a total of 10 kg, was discharged. The same steps were repeated to produce a second blend of 10 kg using the same ingredients. The second blend was then discharged into the same bag as the first blend to obtain 20 kilograms. The formulation may be used for direct compression (e.g., to prepare tablets) or for forming granules (which may be recompacted to form tablets or other solid dosage forms).

The formulations were roller-compacted and then milled to form granulates at Fitzpatrick (The Fitzpatrick Company Europe, Entrepotstraat 8, B-9100 Sint-Niklaas, Belgium) on a pilot scale Chilsonator model IR-520/D6A. The roller compactor was equipped with knurled (grooved) rolls. The feeding auger or horizontal screw was rotating at 12 rpm, and the tamping auger or vertical screw was rotating at 200 rpm. These screw speeds were kept constant throughout the experiments. Compaction pressures were set at 20, 30 or 40 bars to compact the granulate formulations into a ribbon. The resulting gap or distance between the compaction rolls ranged between 1.2 and 1.8 millimeters depending on the compaction pressure applied on the powder/compact and on the granulate formulation being compacted. The mill used was of the type bar rotor rotating at 500 rpm and used in combination with a rasping screen having 1.0 millimeter openings. Approximately 2 kg of granulate were collected at each compaction pressure for each granulate formulation evaluated. Granulate from ribbons compacted at 30 bars was then compressed to form tablets on an ESH Compaction Simulator equipped with 13 millimeter round and flat punches. Compression force was applied only by the upper punch, while the lower punch was fixed during compression. The speed of the compaction simulator was set to obtain a mean compression (vertical) speed for the upper punch of 300 millimeters per second, which corresponds to a dwell time of approximately 6 milliseconds. Dwell time was defined as the time during which more than 90% of the maximum force is applied.

Example 1

A coprocessed microcrystalline cellulose/dibasic calcium phosphate composition was prepared by mixing an aqueous slurry of AVICEL® PH-101 microcrystalline cellulose and Di-Cafos® C92-05 dibasic calcium phosphate anhydrous in a 65:35 weight ratio and spray drying the slurry. The dried agglomerated particulate product had a weight loss on drying (LOD) at 110° C. of 3.1%, a dibasic calcium phosphate (DCP) assay of 33.7%, a loose bulk density (LBD) of 0.44 grams per cubic centimeter, and 15% by weight was the sieve fraction retained on a 200 mesh screen.

A coprocessed microcrystalline cellulose composition was similarly prepared by mixing an aqueous slurry of never dried microcrystalline cellulose (also known as "MCC wet cake") with Di-Cafos® C92-05 dibasic calcium phosphate anhydrous and spray drying the slurry. The dried agglomerated coprocessed particulate product produced from the MCC wet cake had a LOD of 2.9%, a DCP assay of 36.7%, a loose bulk density (LBD) of 0.48 grams per cubic centimeter, and 20% by weight was retained on a 200 mesh screen.

The functionalities of the 65:35 MCC:DCP particulate products and several comparative excipients were assessed as binder excipients for tablets made by both direct compression and roller compaction using a formulation of 69.5% binder, 30.0% Vitamin C, and 0.5% magnesium stearate (lubricant). The comparative excipients evaluated were AVICEL® PH-102 microcrystalline cellulose, a physical blend of 50% by weight of AVICEL® PH-102 microcrystalline cellulose and 50% by weight of SuperTab® 11SD (a direct compression grade of lactose monohydrate), and a physical blend of 65% by weight of AVICEL® PH-102 and 35% by weight of Emcompress® Premium (a direct compression grade of dibasic calcium phosphate dihydrate).

The tablettability of the five formulations in direct compression (the compactibility) is shown in FIG. 1 which plots tablet tensile strength versus tabletting pressure. Both of the coprocessed 65:35 MCC:DCP particulate products show enhanced compactibility (a higher tensile strength at the same tabletting pressure) compared to either of the physical blends of AVICEL® PH-102 and lactose or AVICEL® PH-102 and dibasic calcium phosphate, respectively. AVICEL® PH-102 is very plastically deforming and produces the highest compactibility at tabletting pressures below 110 MPa. Above this pressure, the tensile strength of the formulation containing AVICEL® PH-102 stabilizes at about 2.5 MPa. If the tabletting pressure is increased, for example, to 150 MPa, the tensile strength of the AVICEL® PH-102 formulation may decrease due to defects, such as laminations, which form within the tablet. In comparison, while the coprocessed 65:35 MCC:DCP particulate products had somewhat lower compactibility than AVICEL® PH-102 at lower tabletting pressures, no plateau in tensile strength was observed over the range of pressures tested. Both had a maximum tensile strength of about 4.0 MPa at the highest pressures tested (200 to 225 MPa) showing both a higher maximum tensile strength than AVICEL® PH-102 and no tendency for defects at high pressure.

Figure 2:
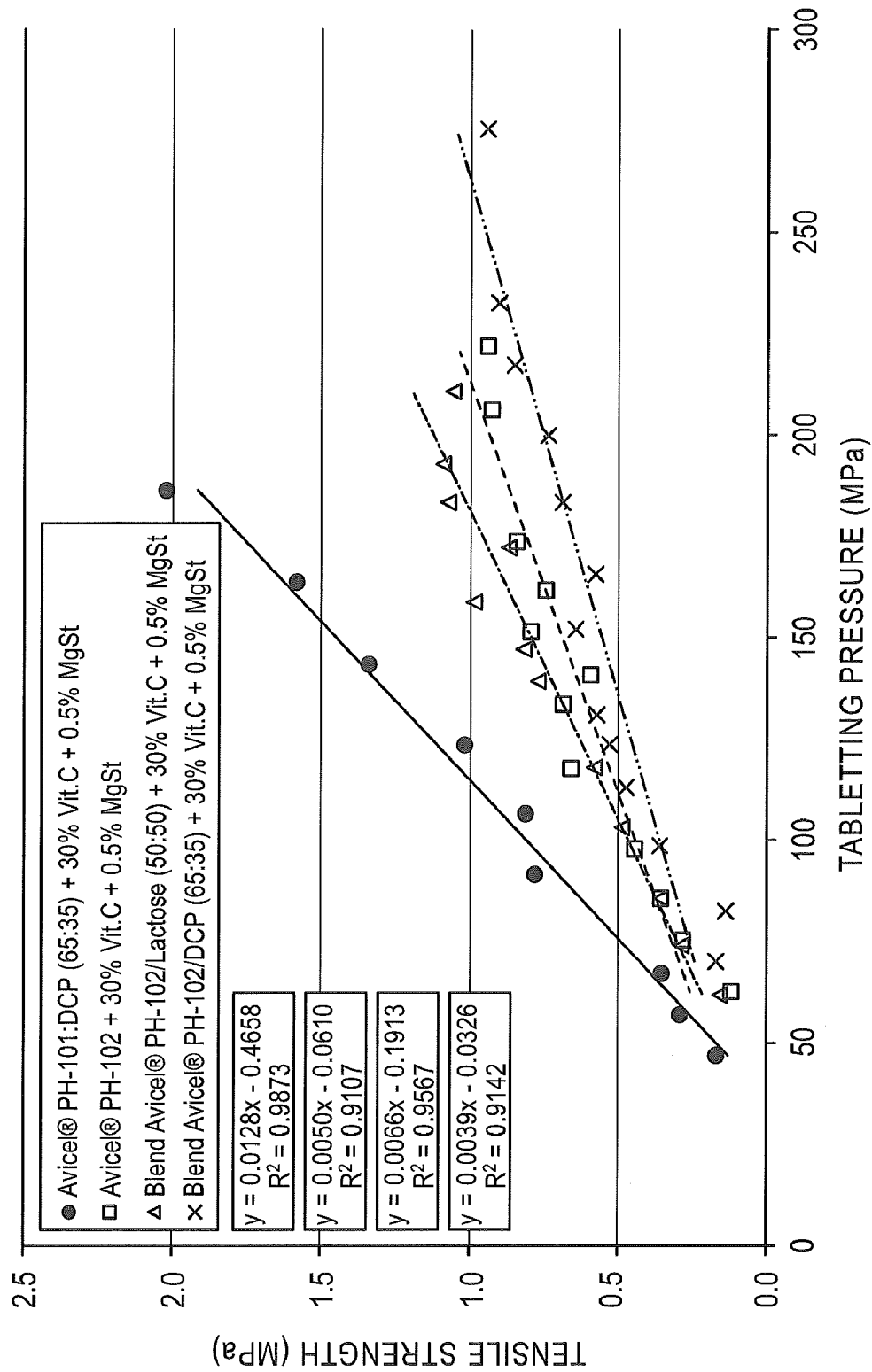
FIG. 2 is a graph comparing the recompactibility of formulations containing Vitamin C, magnesium stearate and various excipients.

The improved recompactibility of the coprocessed MCC: DCP (65:35) particulate product compared with microcrystalline cellulose alone or commercial physical blends was demonstrated by tabletting roller-compacted Vitamin C-containing granules. The excipients tested in the 30% Vitamin C formulation were: the coprocessed 65:35 MCC:DCP particulate product, AVICEL® PH-102 microcrystalline cellulose, a physical blend of AVICEL® PH-102 with lactose, and a physical blend of AVICEL® PH-102 with EMCOMPRESS® Premium dibasic calcium phosphate dihydrate. The 30% Vitamin C granulate formulations containing the different excipients were compacted in a first compaction step (a ribbon was produced by roller compaction at 30 bars), ground to produce granules, and then the granules were compacted in a second compaction step (tabletting). The results are shown in FIG. 2 as a plot of the tablet tensile strength versus tabletting pressure. The coprocessed 65:35 microcrystalline cellulose and dibasic calcium phosphate particulate product provided significantly increased recompactibility. The tensile strength for tablets of the MCC:DCP-containing granulate was higher at each compaction pressure compared to the tensile strength of tablets formed from the corresponding granulates prepared using AVICEL® PH-102, a physical blend of 50:50 AVICEL® PH-102 with lactose monohydrate or a physical blend of 65:35 AVICEL® PH-102 with dibasic calcium phosphate. The tensile strength of tablets that used roller-compacted granulate of the coprocessed MCC:DCP particulate product (65:35) achieved tensile strength values close to 2 MPa, indicative of a robust formulation. The tensile strength values of tablets using the other three granulate formulations barely exceed 1 MPa, which is typical of weak, fragile and friable tablets. The coprocessed MCC:DCP particulate product outperformed the AVICEL® PH-102 alone or the physical blends of AVICEL® PH-102 with either lactose monohydrate or dibasic calcium phosphate.

The superior recompaction performance of the coprocessed microcrystalline cellulose and dibasic calcium phosphate (65:35) particulate product compared to physical blends is characterized by the linear regression ("best fit") of the tablet tensile strength versus tabletting pressure graph, FIG. 2. The linear regression information shown on the figures for each set of tensile strength data is listed in the same order as in the key which indicates which data points are associated with each sample tested. The calculated tensile strengths of tablets produced from the various granulate formulations at 120 MPa tabletting pressure are shown in FIG. 3 based on the respective linear regression reported in FIG. 2. The Vitamin C granulate formulation containing the coprocessed MCC:DCP particulate product is approximately two times more recompactible than granulate formulations containing the comparative physical blends of excipients. The novel 65:35 coprocessed microcrystalline cellulose and dibasic calcium phosphate particulate product is suitable to provide increased tablet robustness compared to typical commercial excipients, to obtain tablets of equivalent hardness at a lower compaction pressure compared to commercial excipients, or to provide increased formulation latitude in the level of active pharmaceutical ingredient or other excipients, or to provide a smaller dosage form with sufficient tensile strength.

Example 2

The recompactibility of coprocessed microcrystalline cellulose and dibasic calcium phosphate particulate products varying in MCC:DCP composition was assessed by tabletting granules obtained from the roller compacted ribbons of granulate formulations composed of 69.5% of the coprocessed particulate product, 30.0% Vitamin C, and 0.5% magnesium stearate.

Coprocessed particulate products were prepared by spray drying aqueous slurries of AVICEL® PH-101 microcrystalline cellulose at 10%, 20%, 22.5%, 30% and 50% of Di-Cafos® C92-04 dibasic calcium phosphate anhydrous. Properties of these dried coprocessed MCC:DCP compositions are reported in Table 1.

TABLE 1

Coprocessed MCC:DCP products with varying levels of DCP

| DCP, % (theoretical) | LOD, % | Sieve Fraction + 200 mesh, % | LBD, g/cc |
|---|---|---|---|
| 10 | 3.6 | 22 | 0.39 |
| 20 | 3.1 | 20 | 0.43 |
| 22.5 | 3.0 | 22 | 0.42 |
| 35 | 2.8 | 19 | 0.46 |
| 50 | 2.6 | 21 | 0.54 |

Figure 4:
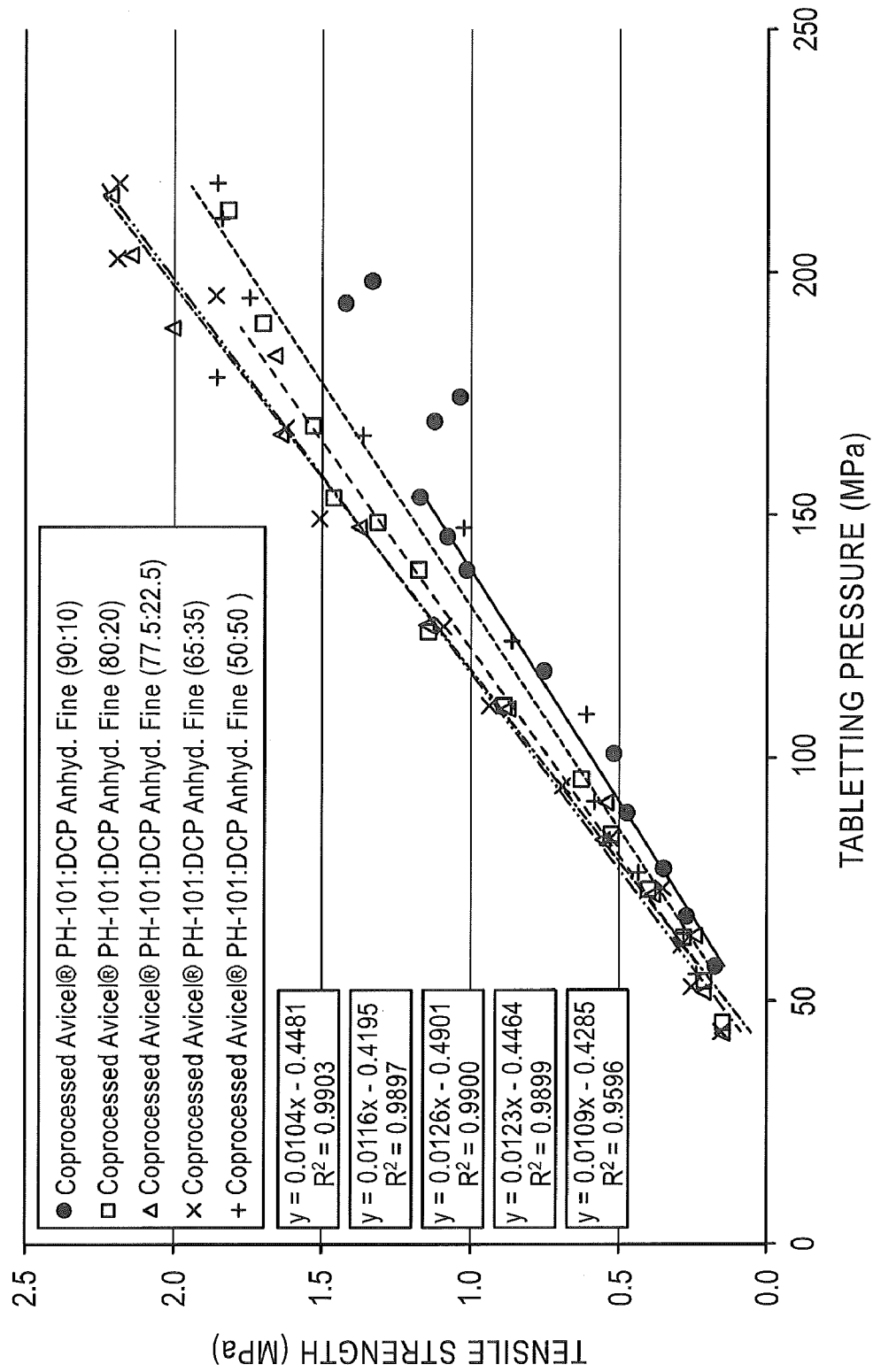
FIG. 4 is a graph comparing the recompactibility of formulations containing Vitamin C, magnesium stearate and coprocessed excipients containing different proportions of anhydrous dibasic calcium phosphate and microcrystalline cellulose.
Figure 5:
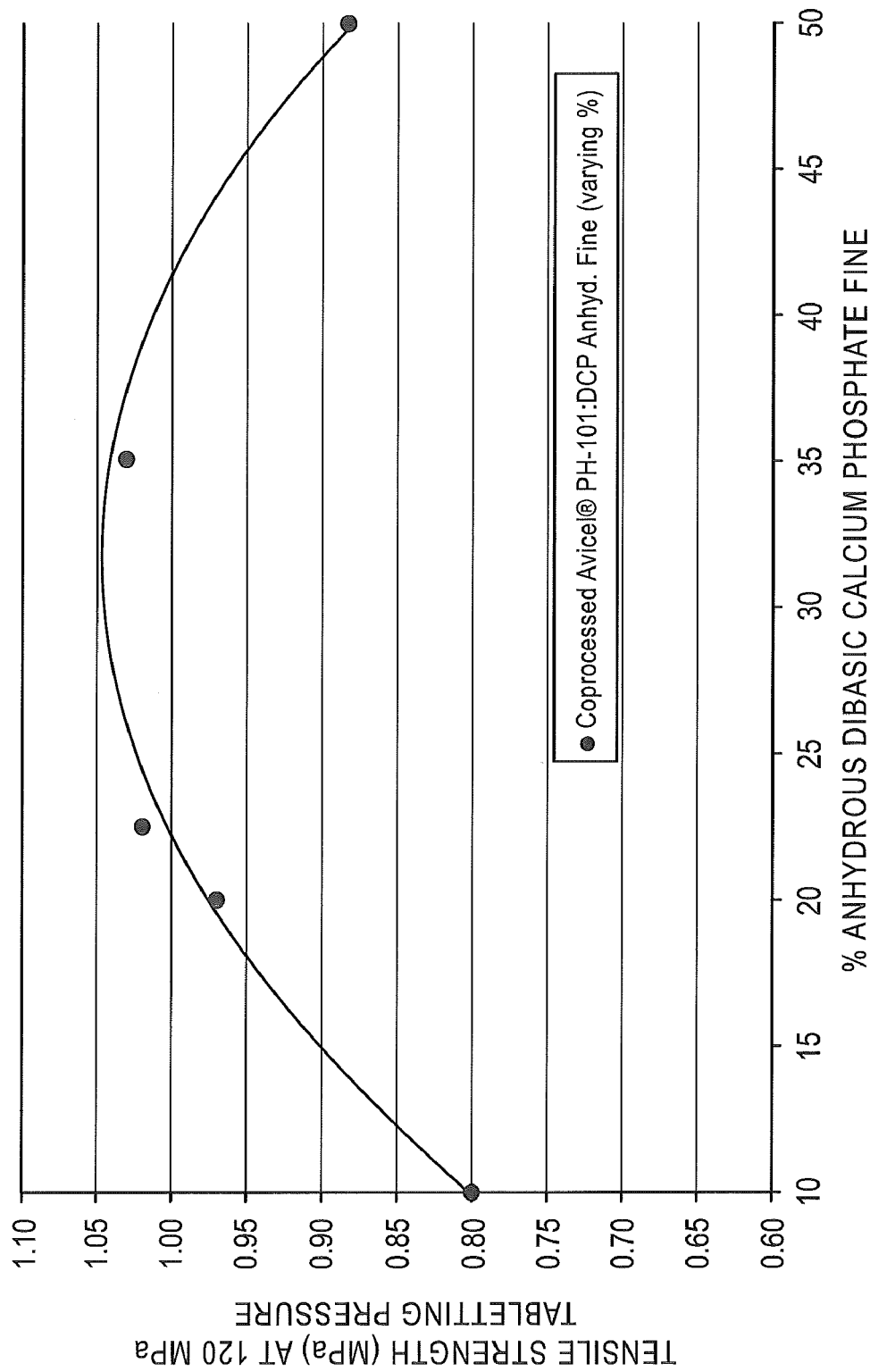
FIG. 5 is a graph comparing the effect of the proportion of anhydrous dibasic calcium phosphate in a coprocessed excipient on the recompactibility of a formulation containing Vitamin C, magnesium stearate and the excipient.

The coprocessed MCC:DCP particulate products were prepared as formulations with 69.5% of the particulate product as the binder, 30.0% Vitamin C, and 0.5% magnesium stearate. The granulate formulations were roller compacted to ribbons at 20, 30 and 40 bars, respectively, following by milling to form granulates. Granulates from ribbons formed by roller compaction at 30 bars were tabletted in the compaction simulator. The data for tensile strength vs. tabletting pressure are shown in FIG. 4 along with the linear regression "best fit" for each composition. FIG. 5 shows the tensile strength at 120 MPa (calculated based on the linear regression data from FIG. 4) versus the percentage of dibasic calcium phosphate in the composition. Coprocessed MCC:DCP particulate products containing 10% or 50% of dibasic calcium phosphate had somewhat lower recompactibility, as characterized by lower tensile strength values obtained by recompacting (tabletting) the roller-compacted granules. In addition, the tablets compacted from granules prepared using coprocessed MCCP:DCP particulate product containing 10% dibasic calcium phosphate showed a tendency towards failure at higher tabletting pressures above 150 MPa. The compaction results showed good recompactibility of granules prepared using coprocessed MCC:DCP particulate products at weight ratios between 80:20 and 65:35.

Figure 6:
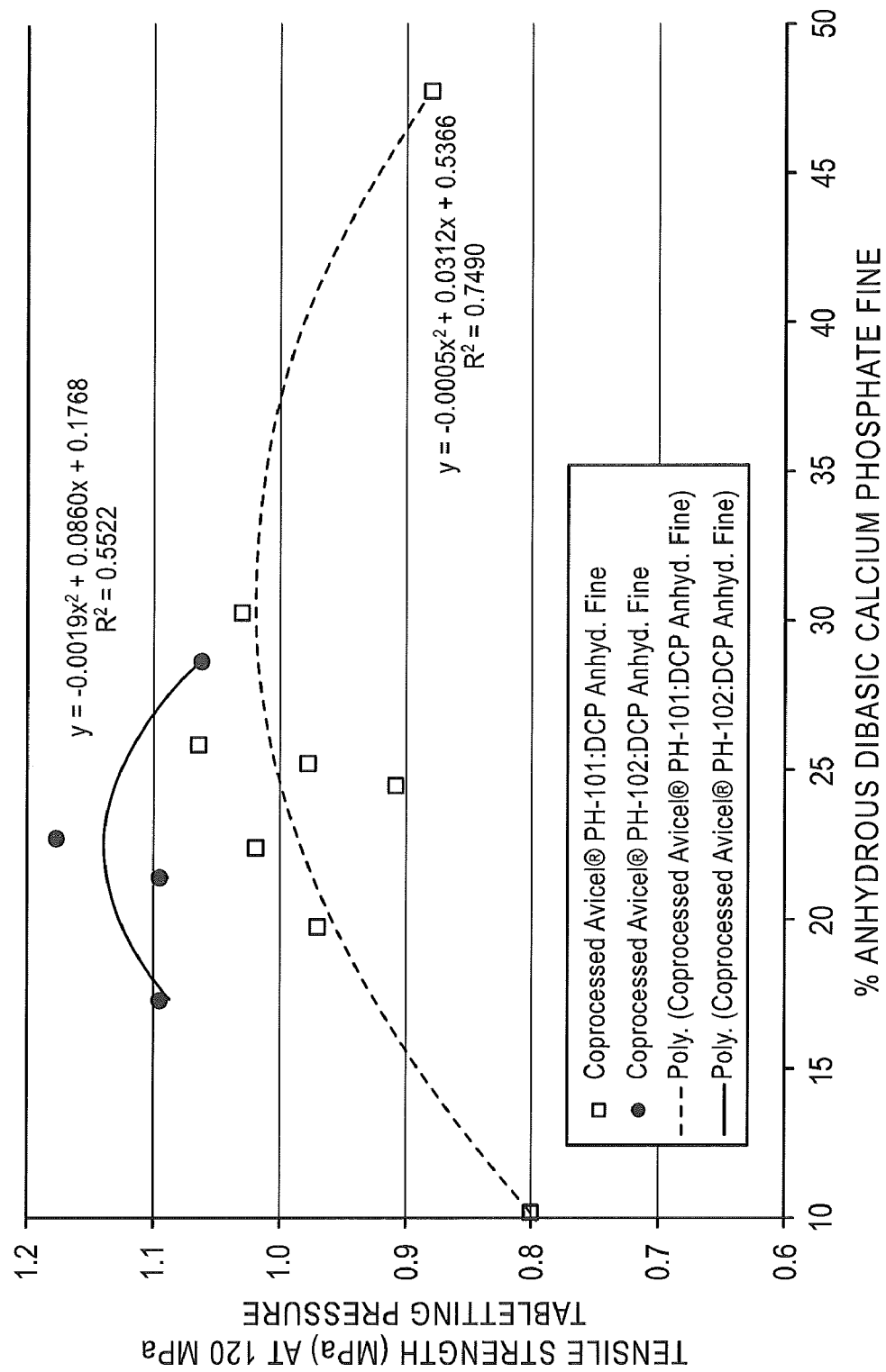
FIG. 6 is a graph comparing the effect of the proportion of anhydrous dibasic calcium phosphate in different coprocessed excipients on the recompactibility of a formulation containing Vitamin C, magnesium stearate and the excipients.

FIG. 6 shows the recompactibility data obtained for tabletted granules produced from roller-compacted MCC:DCP compositions with varying DCP content, prepared by coprocessing of slurries with AVICEL® PH-102 and with AVICEL® PH-101.

Example 3

The recompactibility of coprocessed microcrystalline cellulose and dibasic calcium phosphate particulate products prepared from microcrystalline cellulose of varying particle size was assessed by tabletting granules from ribbons formed by roller compaction (30 bars) of granulate formulations composed of 69.5% of the coprocessed particulate product, 30.0% Vitamin C, and 0.5% magnesium stearate.

Coprocessed excipients were prepared by spray drying aqueous slurries using varying microcrystalline cellulose products (AVICEL® PH-105, AVICEL® PH-101, AVICEL® PH-102 and AVICEL® PH-200) with dibasic calcium phosphate anhydrous. The median particle size of AVICEL® PH-105 is typically about 20 micrometers, AVICEL® PH-101 is about 50 micrometers in median particle size, AVICEL® PH-102 is about 100 micrometers in median particle size, and AVICEL® PH-200, the coarsest grade, is about 200 micrometers in median particle size. Table 2 provides the characteristics of these coprocessed excipients.

TABLE 2

MCC:DCP products (77.5:22.5) with different AVICEL® powders

| MCC type | LOD, % | Sieve Fraction + 200 mesh, % | LBD, g/cc |
|---|---|---|---|
| PH-105 | 3.3 | 20 | 0.42 |
| PH-101 | 3.0 | 22 | 0.42 |
| PH-102 | 3.3 | 24 | 0.41 |
| PH-200 | 3.4 | 50 | 0.38 |

Figure 7:
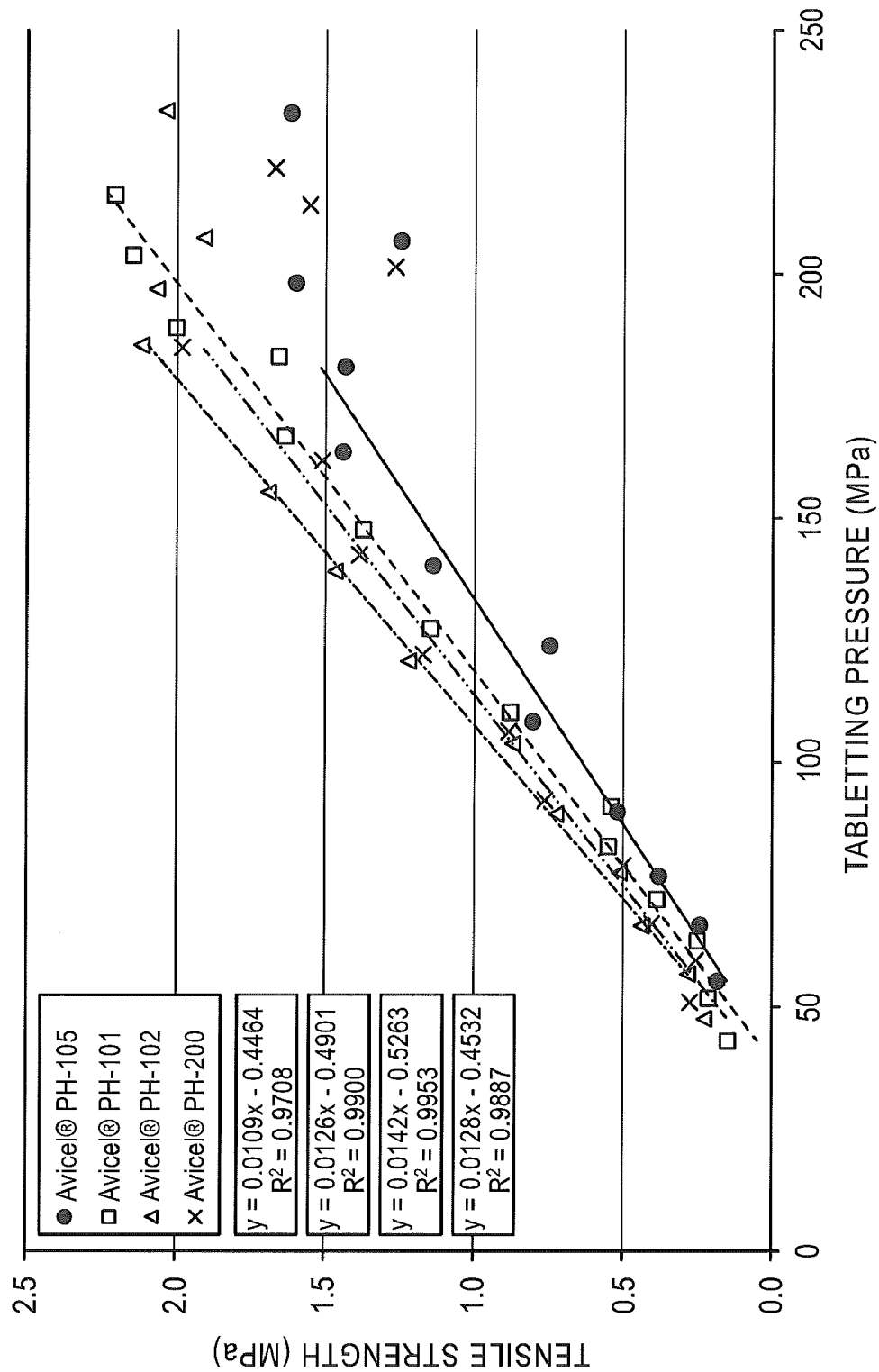
FIG. 7 is a graph showing the effect of varying the type of microcrystalline cellulose used to prepare a coprocessed excipient on the recompactibility of a formulation containing Vitamin C, magnesium stearate and the coprocessed excipient.
Figure 8:
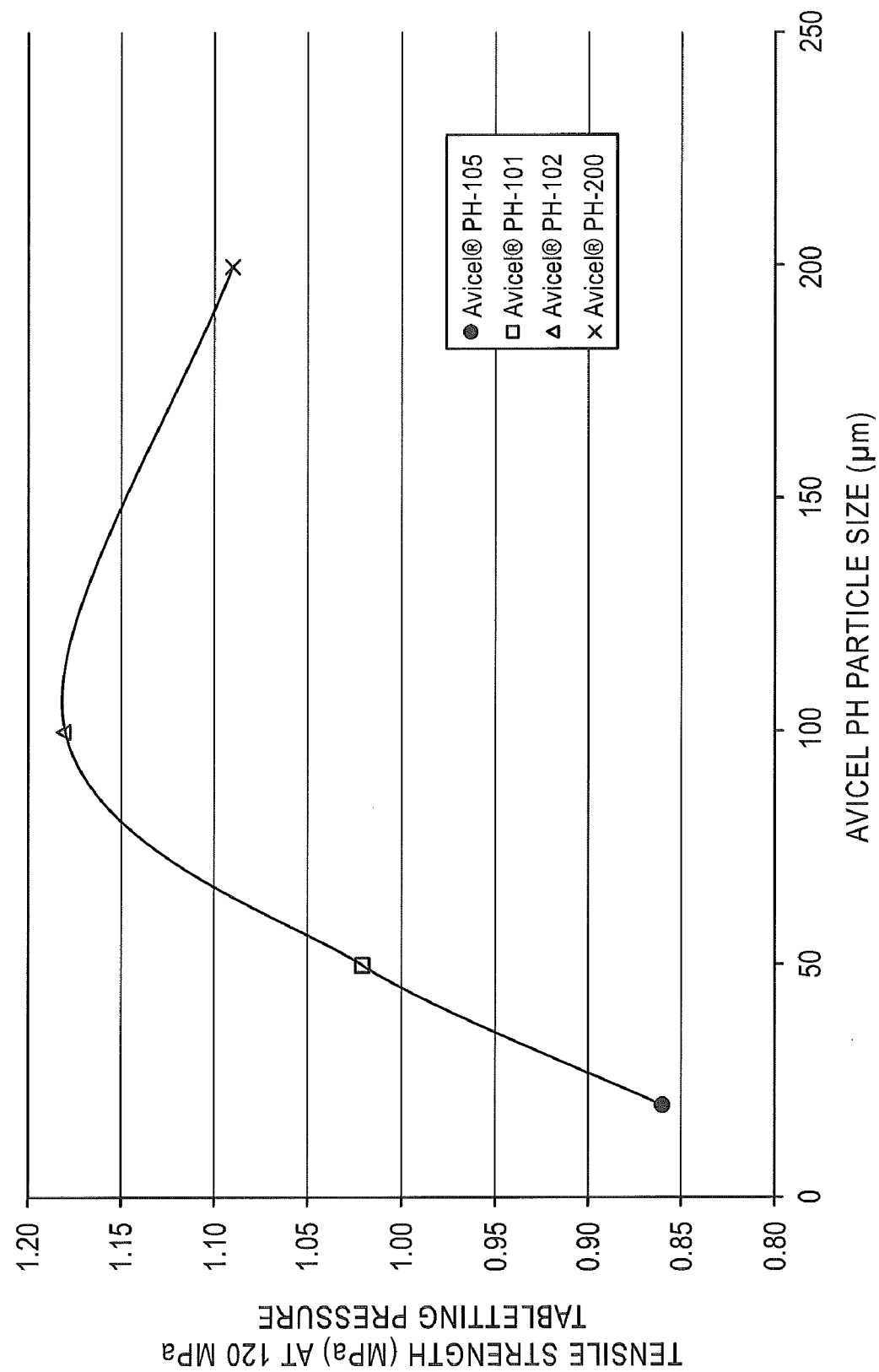
FIG. 8 is a graph showing the effect of microcrystalline cellulose particle size on the recompactibility of a formulation containing Vitamin C, magnesium stearate and a coprocessed excipient prepared using anhydrous dibasic calcium phosphate and microcrystalline cellulose.

The recompactibility or tablettability of the roller compacted granules prepared using these four formulations was tested. FIG. 7 plots the tablet tensile strength versus tabletting pressure data obtained by compaction of 30% Vitamin C granulates. The most recompactible 30% Vitamin C granulate, i.e., the granulate formulation that resulted in the highest tablet tensile strengths, used the coprocessed particulate product made with AVICEL® PH-102. The coprocessed particulate products made with AVICEL® PH-200 or AVICEL® PH-101, respectively, produced granules with similar recompactibility. Coprocessing AVICEL® PH-105 and dibasic calcium phosphate gave a coprocessed particulate product that yielded a less recompactible granulate when tested in a 30% Vitamin C granulate formulation roller compacted at 30 bars. FIG. 8 shows the comparative recompactibility of the coprocessed particulate products based on the calculated tablet tensile strength at a 120 MPa tabletting pressure (using the linear best fit of data from FIG. 7) as a function of the particle size of the AVICEL® PH used in the coprocessed particulate product.

Example 4

The recompactibility of coprocessed microcrystalline cellulose and dibasic calcium phosphate particulate products prepared from varying particle size and composition of dibasic calcium phosphate was assessed by tabletting granules from ribbons formed by roller compaction (30 bars) of granulate formulations composed of 69.5% of the coprocessed particulate product, 30.0% Vitamin C, and 0.5% magnesium stearate.

Coprocessed particulate products were prepared by spray drying aqueous slurries of AVICEL® PH-101 and four grades of dibasic calcium phosphate: Di-Cafos® C92-04 anhydrous fine powder (median particle size of 7 µm), Di-Cafos® C92-05 anhydrous powder (median particle size of 7 µm), Di-Cafos® C92-01 dihydrate powder (median particle size of 14 µm), and Di-Cafos® C92-12 anhydrous coarse (median particle size of 80 µm).

TABLE 3

MCC:DCP products (77.5:22.5) with different DCP powders

| DCP type | LOD, % | Sieve Fraction + 200 mesh, % | LBD, g/cc |
|---|---|---|---|
| C92-04 | 3.0 | 22 | 0.42 |
| C92-05 | 3.9 | 20 | 0.42 |

TABLE 3-continued

MCC:DCP products (77.5:22.5) with different DCP powders

| DCP type | LOD, % | Sieve Fraction + 200 mesh, % | LBD, g/cc |
|---|---|---|---|
| C92-01 | 3.4 | 22 | 0.41 |
| C92-12 | 3.5 | 25 | 0.43 |

Figure 9:
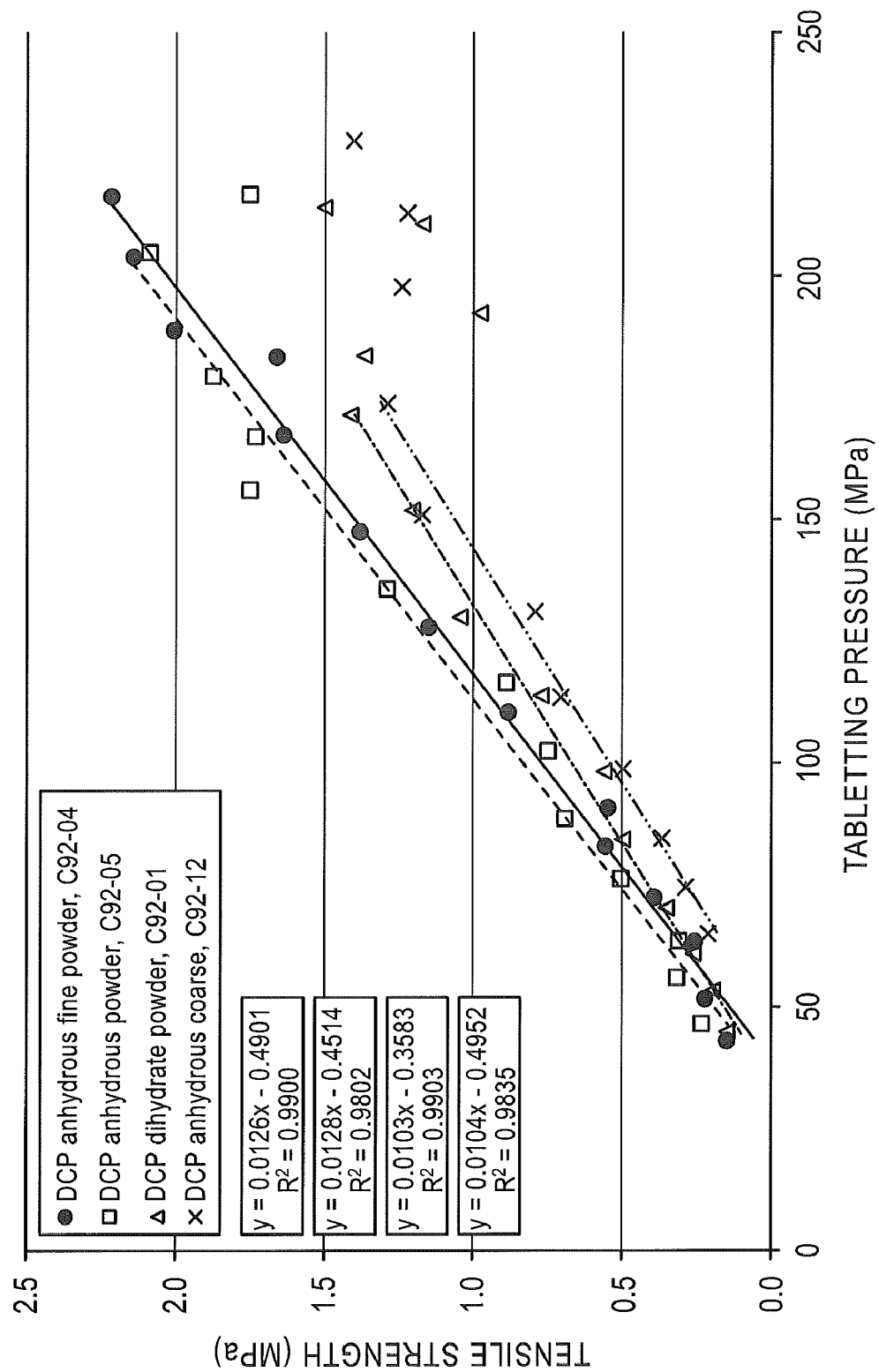
FIG. 9 is a graph showing the effect of different grades of dibasic calcium phosphate on the recompactibility of a formulation containing Vitamin C, magnesium stearate and a coprocessed excipient prepared using dibasic calcium phosphate and microcrystalline cellulose.
Figure 10:
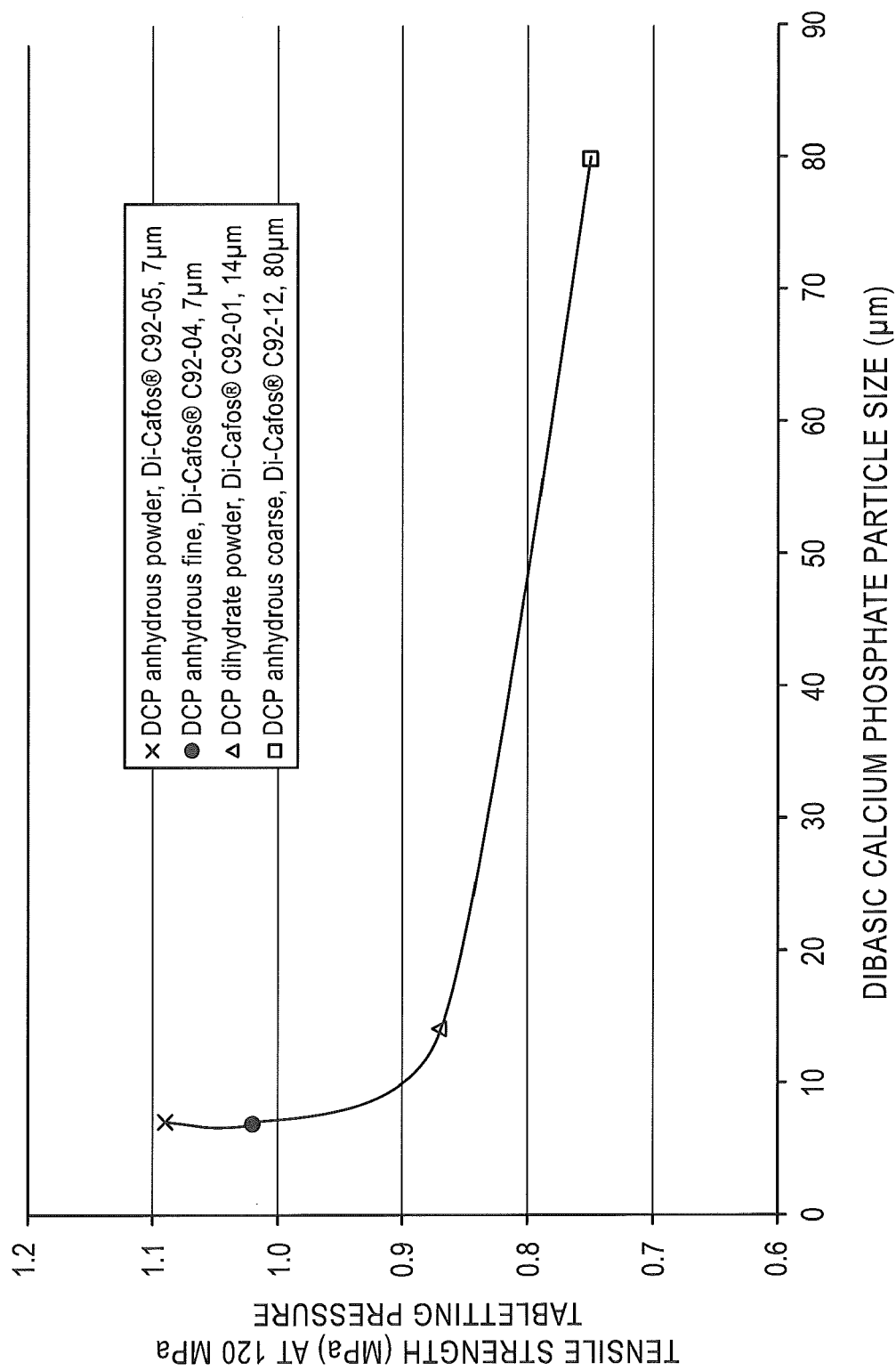
FIG. 10 is a graph showing the effect of dibasic calcium phosphate particle size on the recompactibility of a formulation containing Vitamin C, magnesium stearate and a coprocessed excipient prepared using dibasic calcium phosphate and microcrystalline cellulose.

The recompactibility or tablettability of the roller compacted granules prepared using these four formulations is illustrated in FIG. 9 which plots tablet tensile strength versus tabletting pressure. The most recompactible 30% Vitamin C granulates, i.e. the granulate formulation that resulted in the higher tablet tensile strengths, used the coprocessed particulate product made with 77.5% AVICEL® PH 101 and 22.5% dibasic calcium phosphate with a median particle size of 7 microns. Particulate products produced by coprocessing 77.5% AVICEL® PH-101 with 22.5% dibasic calcium phosphate with larger particle sizes of 14 microns and 80 microns gave a coprocessed particulate product that yielded a less recompactible granulate when tested in a 30% Vitamin C granulate formulation roller compacted at 30 bars. FIG. 10 shows the comparative recompactibility of the coprocessed particulate products based on the calculated tablet tensile strength at a 120 MPa tabletting pressure (using the linear best fit of data from FIG. 9) as a function of the dibasic calcium phosphate particle size used in the coprocessed composition.

Example 5

The recompactibility of coprocessed microcrystalline cellulose and dibasic calcium phosphate particulate products having a median particle size of about 40 to 50 microns or about 70 microns was assessed by tabletting granules from ribbons formed by roller compaction (30 bars) of formulations composed of 69.5% of the coprocessed particulate product, 30.0% Vitamin C, and 0.5% magnesium stearate.

Coprocessed particulate products were prepared by spray drying aqueous slurries of AVICEL® PH-101 or AVICEL PH-102 with Di-Cafos® C92-04 dibasic calcium phosphate anhydrous and changing the spray drying process conditions to produce varying particle sizes. The characteristics of these particulate products are listed in Table 4.

TABLE 4

MCC:DCP products (77.5:22.5) with Varying Spray Dried Particle Size

| MCC type | Particle size Malvern D50, microns | LOD, % | Sieve Fraction + 200 mesh, % | LBD, g/cc |
|---|---|---|---|---|
| PH-101 | 38 | 3.0 | 22 | 0.42 |
| PH-101 | 72 | 3.9 | 61 | 0.45 |
| PH-102 | 47 | 3.3 | 24 | 0.41 |
| PH-102 | 73 | 3.5 | 52 | 0.42 |

Figure 11:
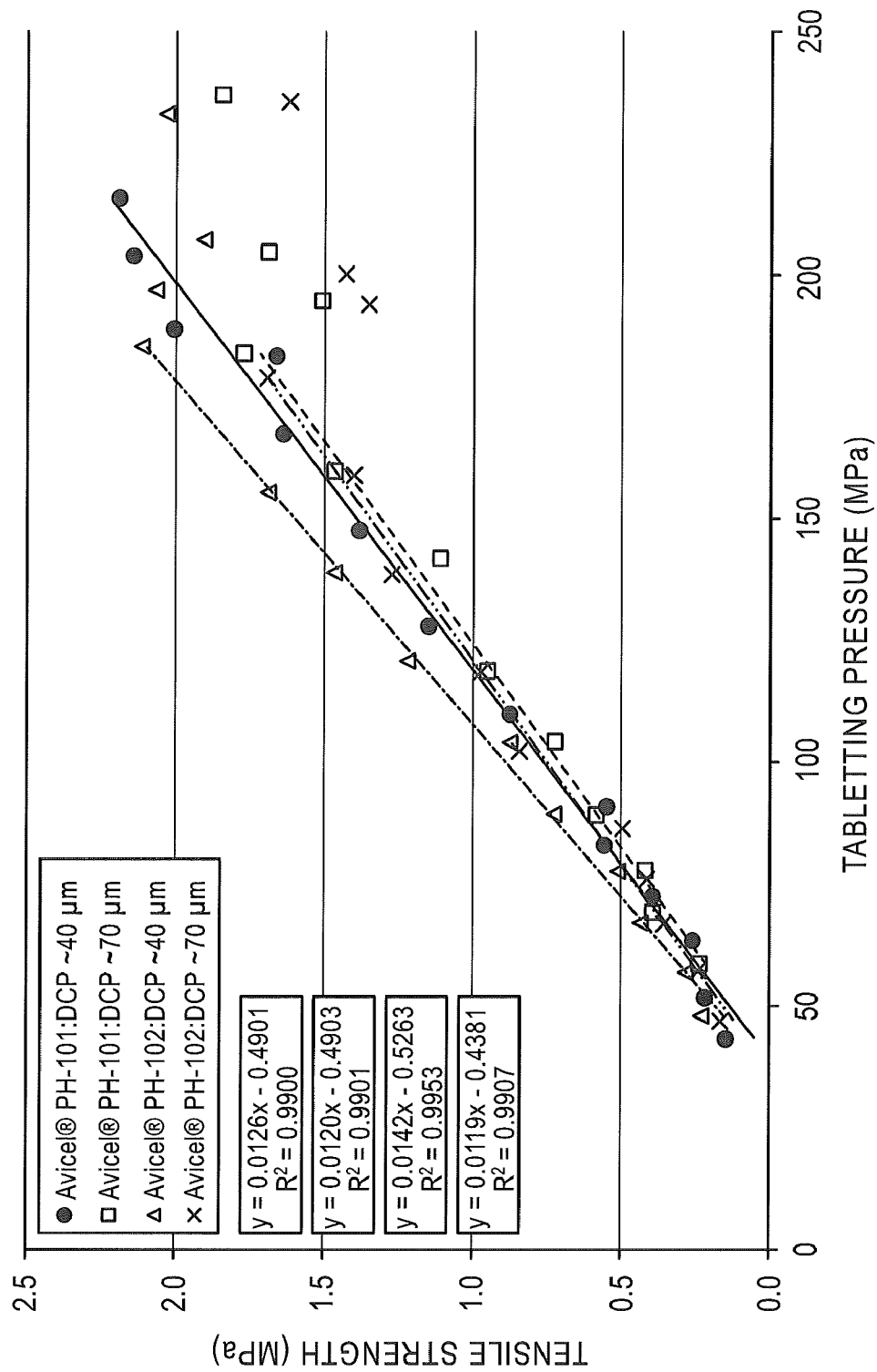
FIGS. 11 and 12 are graphs showing the influence of the particle size of particulate product in accordance with the invention on recompactibility performance of granules prepared using the particulate product.
Figure 12:
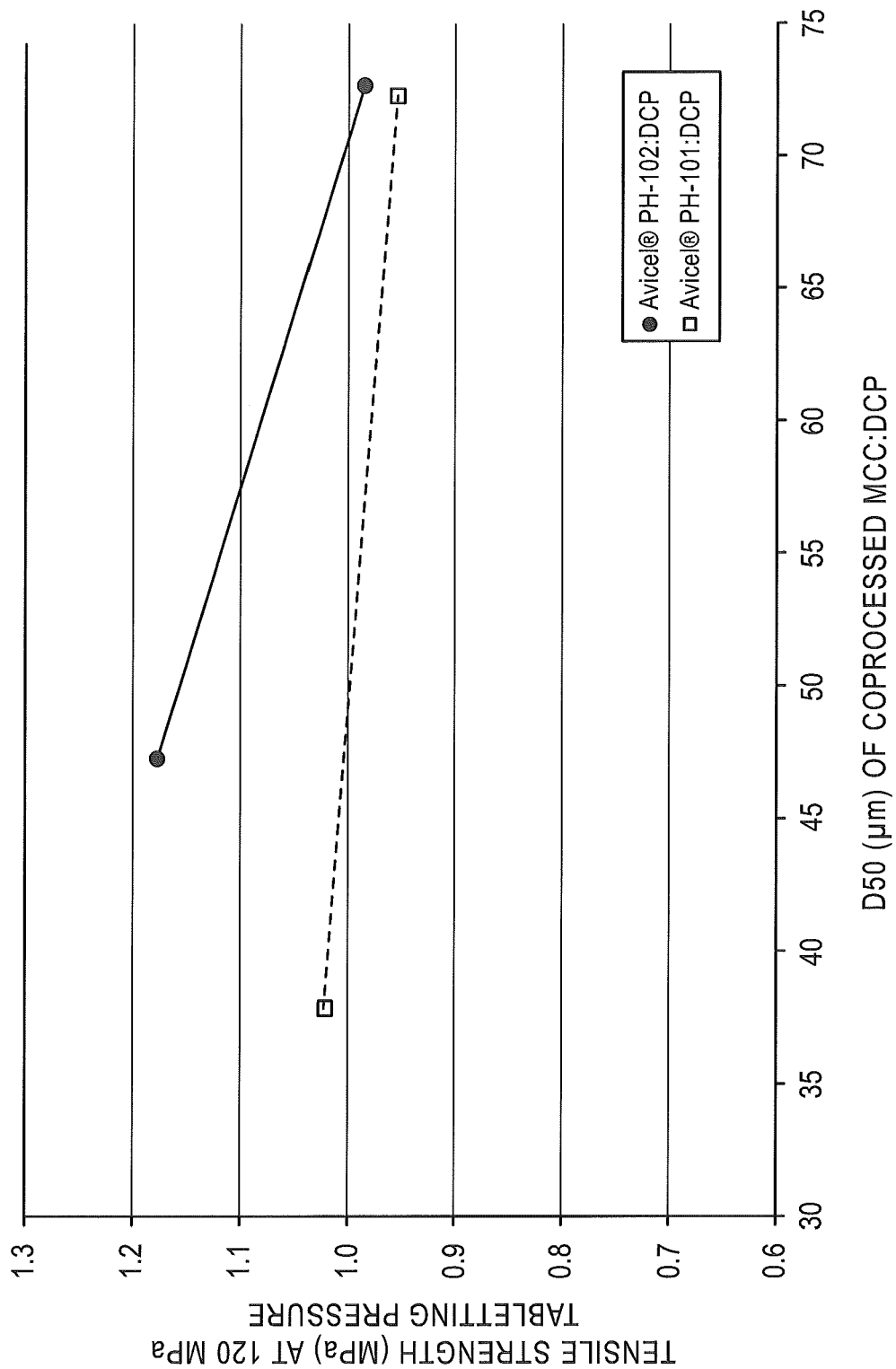

FIG. 11 plots the tensile strength of 30% Vitamin C tablets (produced using granules from ribbons formed by roller compaction at 30 bars) vs. tabletting pressure. Recompactibility was higher for granules prepared from particulate products having particle sizes of 35 to 50 micrometers; increasing the particle size to about 70 micrometers decreased recompactibility. The influence of particle size on granule recompactibility is illustrated in FIG. 12, which plots tablet tensile strength at a tabletting pressure of 120 MPa (calculated based on the linear regression "best fit" of the data in FIG. 11) versus the particle size (D50 as measured by laser diffraction using a Malvern Mastersizer 2000) of the coprocessed MCC:DCP particulate product.

Example 6

The recompactibility of coprocessed particulate products at MCC:DCP ratios of 75:25 using fine DCP was assessed by tabletting granules obtained from ribbons formed by roller compaction (30 bars) of granulate formulations composed of 69.5% MCC:DCP excipient, 30.0% Vitamin C, and 0.5% magnesium stearate.

Coprocessed MCC:DCP particulate products were prepared by spray drying aqueous slurries of AVICEL® PH with Di-Cafos C92-04 dibasic calcium phosphate anhydrous as received and after milling the DCP to a median particle size of 2 microns. Table 5 lists the characteristics of these particulate products.

TABLE 5

MCC:DCP Participate Products (75:25)

| MCC type | DCP Assay | DCP PS, microns | Particle size Malvern D50, microns | LOD, % | Sieve Fraction + 200 mesh, % | LBD, g/cc |
|---|---|---|---|---|---|---|
| PH-102 | 26 | 7 | 42 | 4.1 | 12 | 0.31 |
| PH-102 | 25 | 7 | 42 | 3.9 | 11 | 0.32 |
| PH-102 | 25 | 7 | 43 | 4.4 | 14 | 0.31 |
| PH-102 | 25 | 2 | 44 | 3.6 | 22 | 0.38 |
| PH-101 | 25 | 2 | 36 | 3.6 | 18 | 0.39 |

Figure 13:
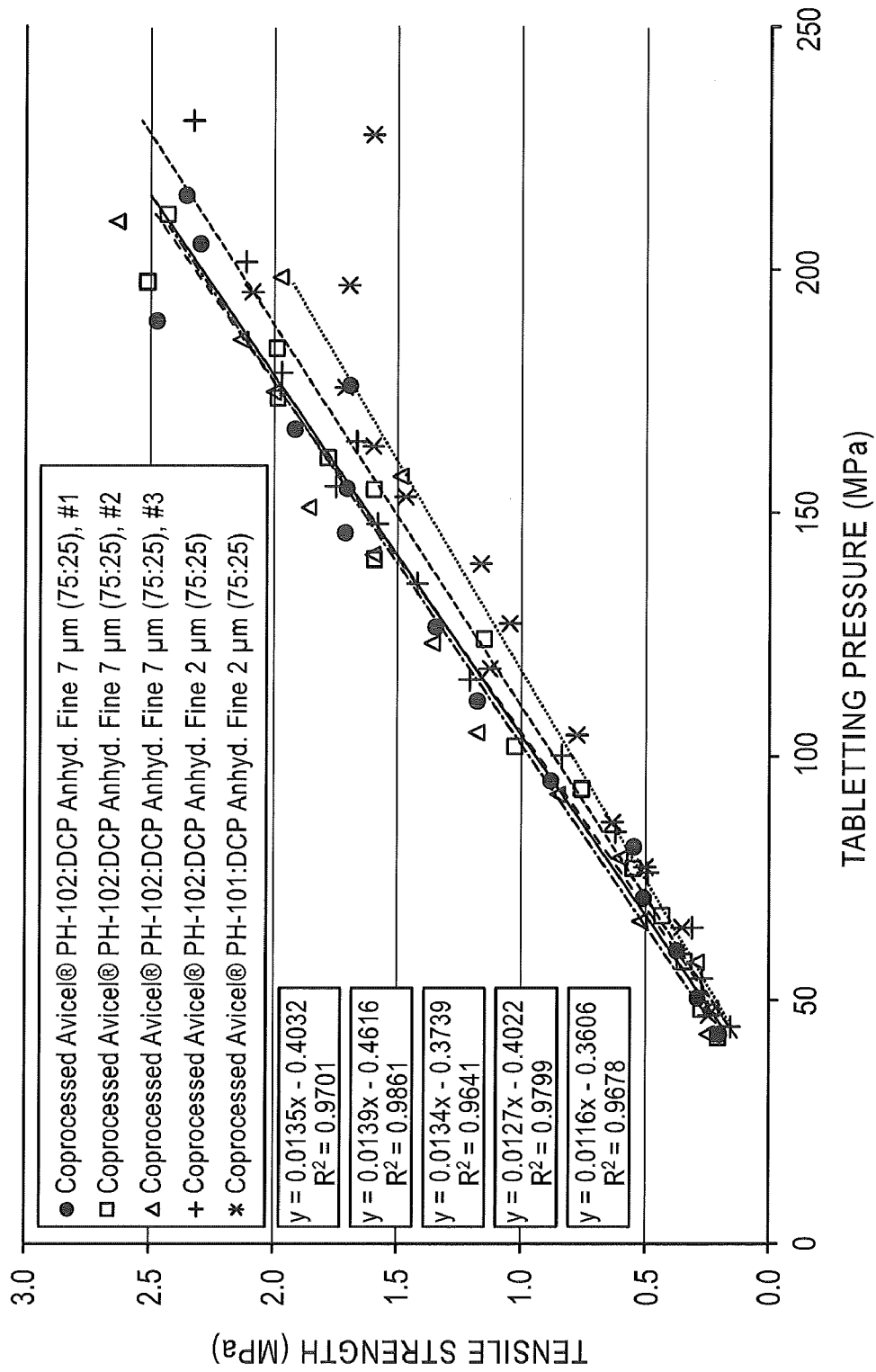
FIG. 13 is a graph showing the lot-to-lot reproducibility in recompactibility performance of granules prepared with coprocessed particulate product in accordance with the invention.

FIG. 13 shows excellent lot-to-lot reproducibility of recompactibility performance.

Example 7

Friability of roller-compacted ribbons of the MCC:DCP particulate product (75:25) was assessed compared to physical blends of microcrystalline cellulose with lactose anhydrous (50:50) and microcrystalline cellulose with dibasic calcium phosphate anhydrous (65:35 and 75:25).

The coprocessed MCC:DCP particulate product (75:25) was prepared by spray drying an aqueous slurry of AVICEL® PH-102 with Di-Cafos® C92-04 dibasic calcium phosphate anhydrous. Physical blend samples were prepared using appropriate weight ratios of AVICEL® PH-101 with SuperTab® 21AN or Anhydrous EMCOMPRESS® as the 69.5% excipient portion of the 30% Vitamin C granulate formulation.

Ribbons were produced by roller compaction of 30% Vitamin C granulate formulations at 20, 30 and 40 bars. Ribbon portions having an approximate ribbon width of five centimeters were broken into pieces approximately 2.5 to 3.5 centimeters in length. Three pieces of ribbon (about 10 to 20 grams in total weight) were initially de-dusted on a 1000 micron sieve with a soft brush and then weighed. The de-dusted pieces were introduced into the drum of a Pharma test PTF1 friability tester for 100 rotations (four minutes at 25 rotations per minute). The contents of the drum were removed after testing and the powder fraction separated on the 1000 micron sieve. The oversize fraction remaining on the sieve was weighed and compared to the initial weight of the ribbon after de-dusting.

Table 6 shows that the coprocessed MCC:DCP particulate product (75:25) produced robust compacted ribbons with lower friability at each compaction pressure (20, 30 and 40 bars) compared to the physical blends of AVICEL® PH-101 with SuperTab® 21AN (50:50) or with Anhydrous EMCOMPRESS® (65:35 and 75:25). Robust ribbons of comparable friability can be obtained for the coprocessed MCC:DCP particulate product at a lower compaction pressure than for the blend formulations. The particulate product in accordance with the present invention unexpectedly provides both reduced ribbon friability and improved recompactibility.

TABLE 6

Ribbon Friability of MCC:DCP Particulate Product (75:25) and Physical Blends

| Excipient | Ratio | Compaction pressure, bars | Initial, g | Final, g | Ribbon friability, % |
|---|---|---|---|---|---|
| MCC:DCP coprocessed | 75:25 | 20 | 14.96 | 12.64 | 15.5 |
| MCC:lactose blend | 50:50 | 20 | 15.56 | 11.78 | 24.3 |
| MCC:DCP blend | 65:35 | 20 | 15.23 | 11.46 | 24.8 |
| MCC:DCP blend | 75:25 | 20 | 14.97 | 11.48 | 23.3 |
| MCC:DCP coprocessed | 75:25 | 30 | 15.43 | 13.55 | 12.2 |
| MCC:lactose blend | 50:50 | 30 | 16.28 | 12.89 | 20.8 |
| MCC:DCP blend | 65:35 | 30 | 13.98 | 11.16 | 20.2 |
| MCC:DCP blend | 75:25 | 30 | 13.21 | 11.02 | 16.6 |
| MCC:DCP coprocessed | 75:25 | 40 | 14.40 | 13.23 | 8.1 |
| MCC:lactose blend | 50:50 | 40 | 16.90 | 13.99 | 17.2 |
| MCC:DCP blend | 65:35 | 40 | 16.22 | 13.53 | 16.6 |
| MCC:DCP blend | 75:25 | 40 | 16.33 | 14.01 | 14.2 |

Example 8

The recompactibilities of coprocessed particulate products at MCC:DCP ratios of 80:20, 75:25 and 65:35 and physical blends of the same composition were assessed by tabletting granules produced from ribbons formed by roller compaction (30 bars) of granulate formulations composed of 69.5% of the particulate product or blend as the excipient, 30.0% Vitamin C, and 0.5% magnesium stearate.

Figure 14:
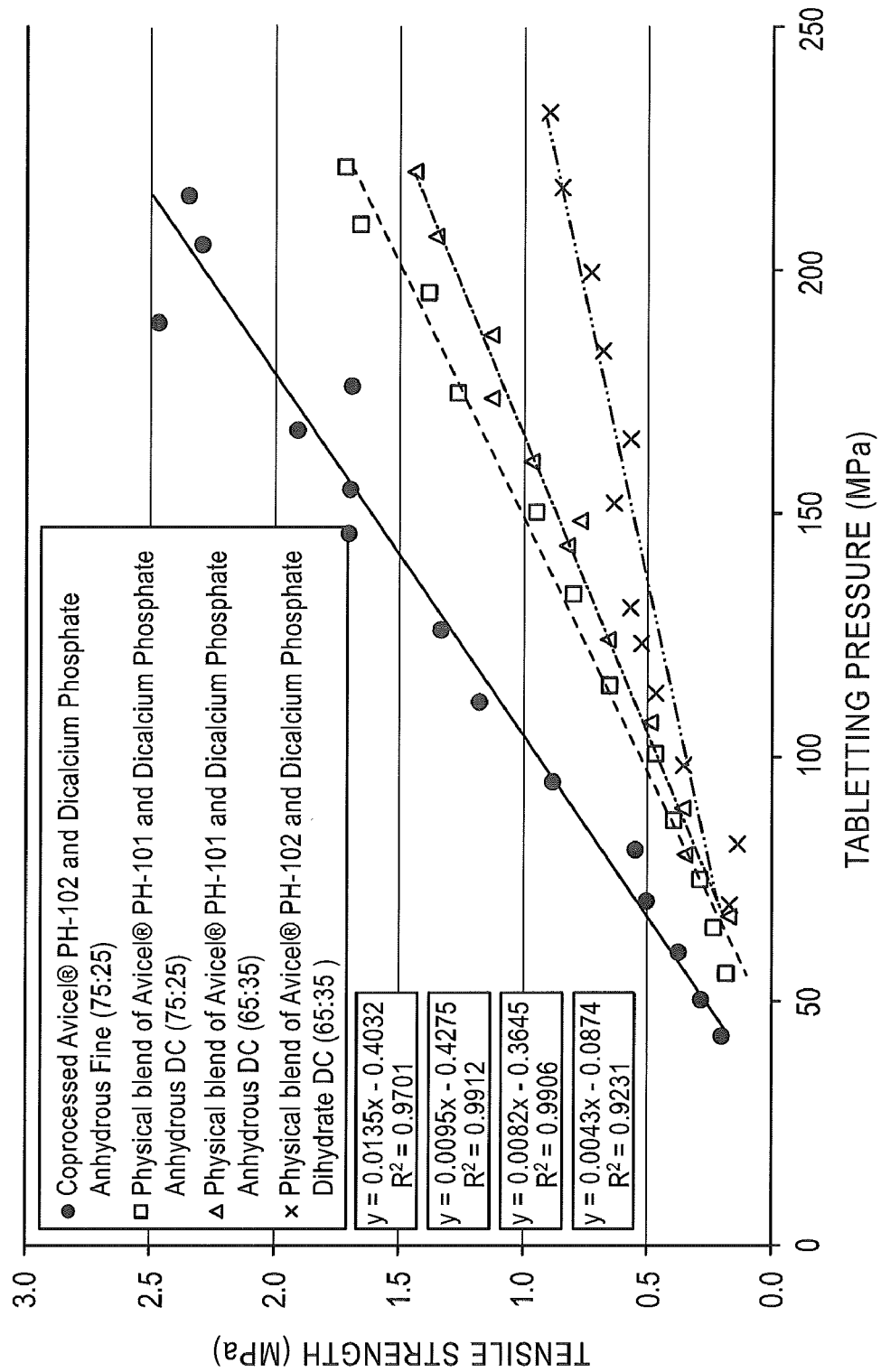
FIGS. 14 and 15 are graphs comparing the recompactibility performance of granules prepared using coprocessed particulate product in accordance with the invention with the performance of granules prepared using corresponding physical blends of microcrystalline cellulose and dibasic calcium phosphate.
Figure 15:
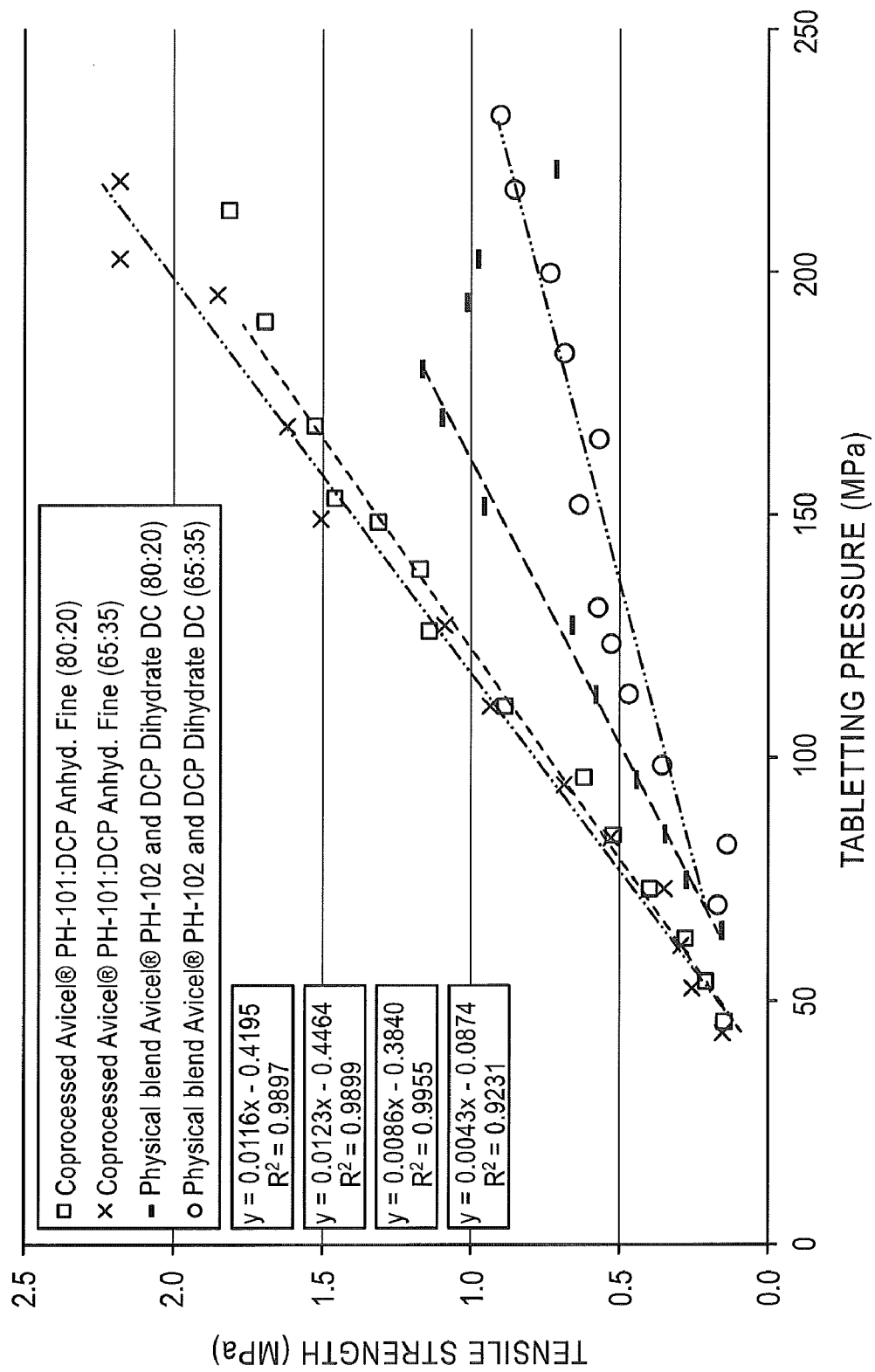

Physical blend samples were prepared at MCC:DCP ratios of 75:25 or 65:35 for the 69.5% excipient portion of the 30% vitamin C granulate formulation. The physical blends used AVICEL® PH-101 with Anhydrous EMCOMPRESS®, direct compression grade of dibasic calcium phosphate anhydrous or AVICEL® PH-102 with EMCOMPRESS® Premium, a direct compression grade of dibasic calcium phosphate dihydrate (FIG. 14). Physical blend samples were also prepared with AVICEL® PH-102 and EMCOMPRESS® Premium at 80:20 and 65:35 weight ratios, respectively, in the 69.5% excipient portion in the 30% Vitamin C granulate formulations (FIG. 15).

Coprocessed MCC:DCP particulate products were prepared by spray drying aqueous slurries of AVICEL® PH-101 with Di-Cafos® C92-04 dibasic calcium phosphate anhydrous (at ratios of 80:20 and 65:35, respectively, FIG. 15), and AVICEL® PH-102 with Di-Cafos® C92-04 dibasic calcium phosphate anhydrous at 75:25 (FIG. 14). The characteristics of these particulate products are listed in Table 7.

TABLE 7

Coprocessed MCC:DCP with Varying Ratios and Components

| MCC type | MCC:DCP | LOD, % | Sieve Fraction + 200 mesh, % | LBD, g/cc |
|---|---|---|---|---|
| PH-101 | 80:20 | 3.1 | 20 | 0.43 |
| PH-101 | 65:35 | 2.8 | 19 | 0.46 |
| PH-102 | 75:25 | 4.1 | 12 | 0.31 |

The granulate formulations were roller-compacted at 30 bars to form a ribbon, subsequently ground to produce granules, and recompacted when the granules were tabletted.

Recompactibility data are reported in FIG. 14 and FIG. 15 as the tablet tensile strength versus tabletting pressure. FIG. 14 shows that the recompactibility of the coprocessed MCC:DCP particulate product spray-dried from an aqueous slurry of 75:25 AVICEL® PH-102 and Di-Cafos® 92-04 anhydrous was significantly higher than that of the three physical blends at the 75:25 or 65:35 compositions. FIG. 15 shows that the coprocessed MCC:DCP particulate products at both the 80:20 and 65:35 ratios are significantly more recompactible than the corresponding physical blends.

Example 9

The performance and lubricant sparing ability of the coprocessed MCC:DCP particulate product (75:25) were assessed in comparison with microcrystalline cellulose and physical blends of microcrystalline cellulose with lactose and DCP excipients by tabletting granules from ribbons formed by roller compaction (30 bars) of granulate formulations using 99% excipient and 1.0% magnesium stearate.

Figure 16:
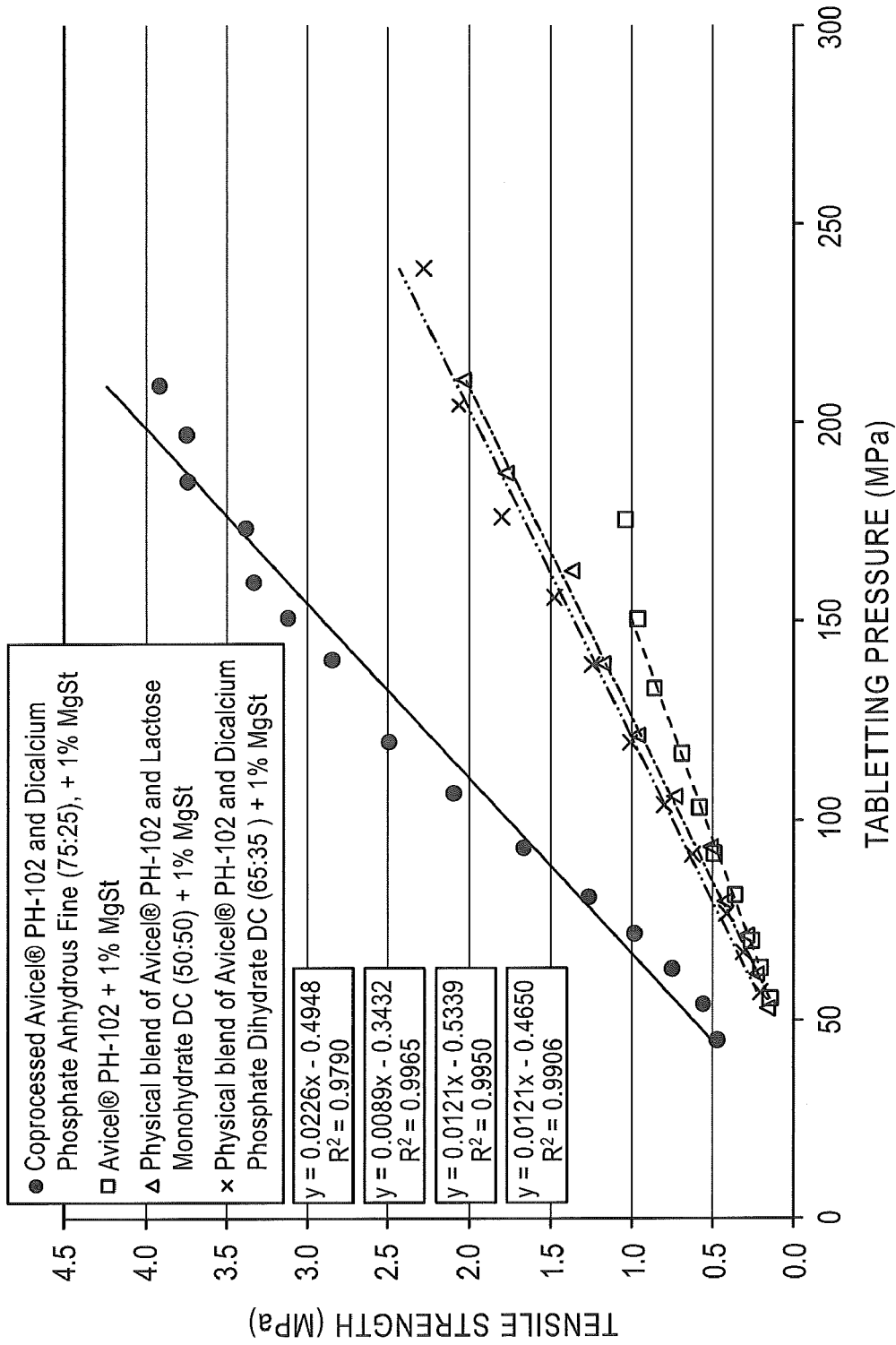
FIG. 16 is a graph comparing the recompactibility performance of granules prepared using various excipients.

Compactibility data obtained by tabletting granules formed from roller-compacted granulate compositions are reported in FIG. 16 as the tablet tensile strength versus tabletting pressure. The coprocessed MCC:DCP particulate product (75:25) showed improved recompactibility and significantly better lubricant sparing performance compared to AVICEL® PH-102 alone or physical blends of AVICEL® PH-102 with SuperTab® 11SD lactose monohydrate or EMCOMPRESS® Premium dibasic calcium phosphate dihydrate direct compression excipients, respectively.

Example 10

Figure 17:
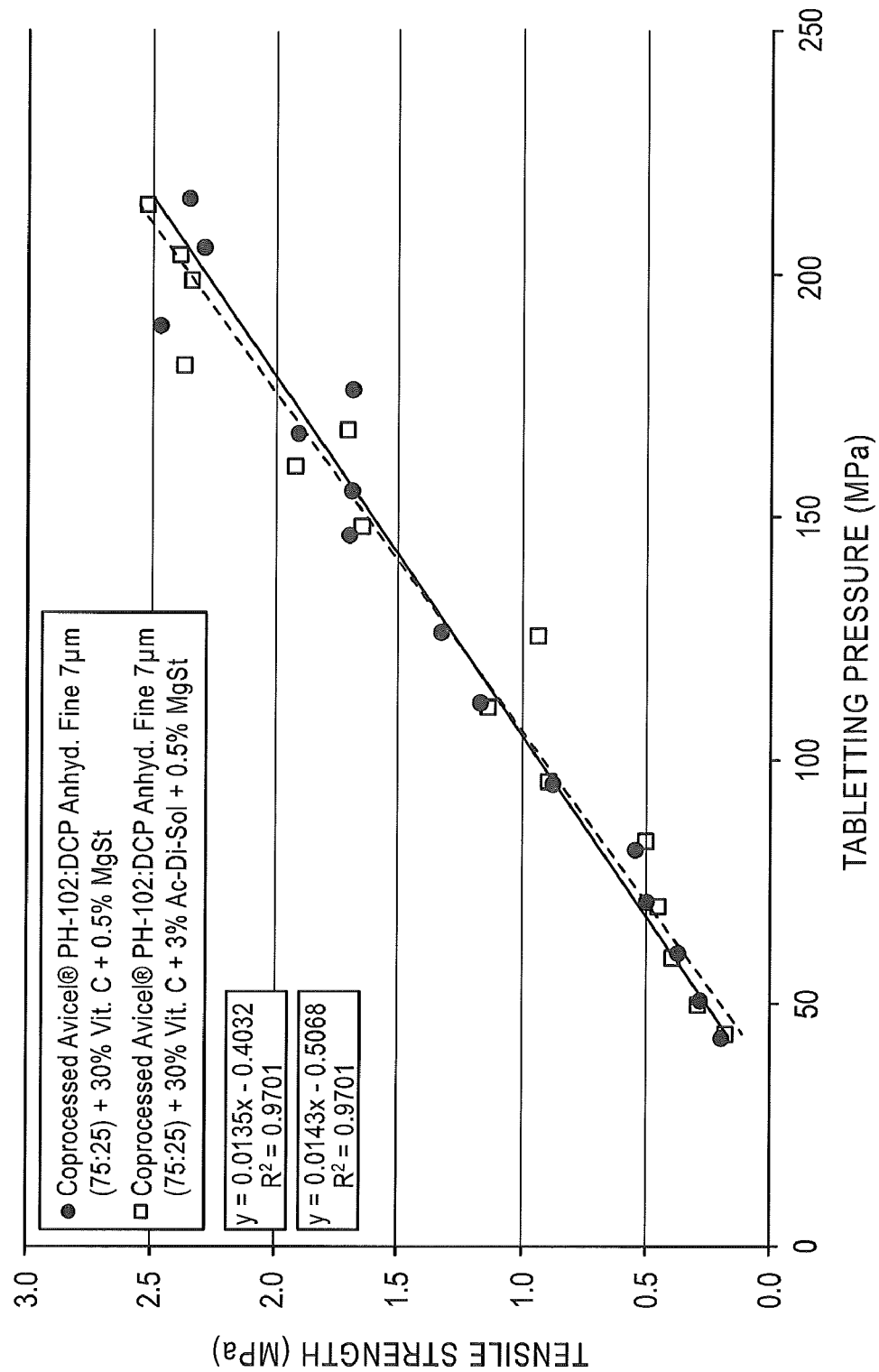
FIG. 17 is a graph showing the recompactibility of granulate formulations prepared using coprocessed particulate products in accordance with the invention, both with and without a disintegrant.

Recompactibility of the coprocessed MCC:DCP particulate product (75:25) was assessed by tabletting granules obtained from ribbons formed by roller compaction (30 bars) of 30% Vitamin C granulate formulations with and without 3% of Ac-Di-Sol® crocarmellose sodium and 0.5% magnesium stearate. The tabletting data are reported in FIG. 17 with the linear regression "best fit" of the data. The coprocessed MCC:DCP product showed substantially the same recompactibility with and without the disintegrant.

Comparative Example 1

Recompactibility (recompaction performance) was assessed by tabletting granules from ribbons formed by roller compaction (30 bars) of 30% Vitamin C granulate formulations of coprocessed MCC:DCP particulate product (15:85) and MicroceLac®, a direct compression grade of coprocessed microcrystalline cellulose with lactose monohydrate (25:75), and the corresponding physical blends of AVICEL®

PH-101 with direct compression grade excipients Anhydrous EMCOMPRESS® (15:85) and SuperTab® 21AN (25:75), respectively.

Coprocessed MCC:DCP particulate products (15:85) were prepared by spray drying aqueous slurries of AVICEL® PH-102 with Di-Cafos® C92-04 dibasic calcium phosphate anhydrous. The characteristics of such a particulate product are shown in Table 8.

TABLE 8

Coprocessed MCC:DCP (15:85)

| MCC | DCP | MCC:DCP | LOD, % | Sieve Fraction + 200 mesh, % | LBD, g/cc |
|---|---|---|---|---|---|
| PH-102 | C92-04 | 15:85 | 0.6 | 4 | 6.2 |

Figure 18:
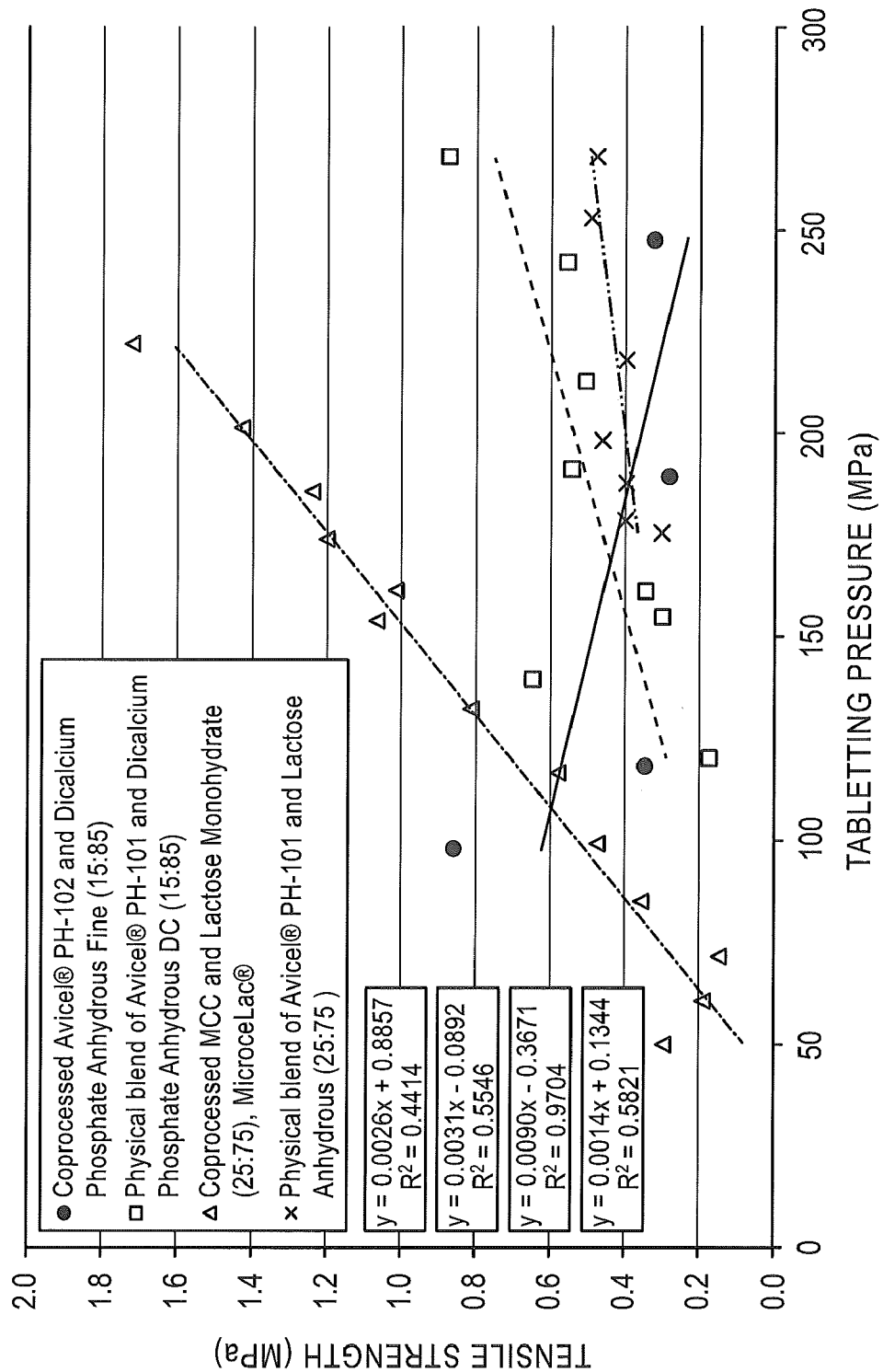
FIGS. 18-20 are graphs comparing the recompactibility performance of granules prepared using various excipients.

The tablettability data are reported in FIG. 18. Recompacting 30% Vitamin C granules of the coprocessed MCC:DCP particulate product (15:85) resulted in a very friable tablet at the lowest tabletting pressure (97.6 MPa) while tensile strengths in the range of 0.2 to 0.4 MPa were observed at tabletting pressures greater than about 120 MPa to 250 MPa. The physical blend of MCC and DCP was tested at tabletting pressures from 51.5 MPa to 267.6 MPa, but required tabletting pressures above 120 MPa to obtain a tablet of sufficient hardness (at least 10 N, corresponding to a tensile strength of at least 0.2 MPa).

Example 11

Figure 19:
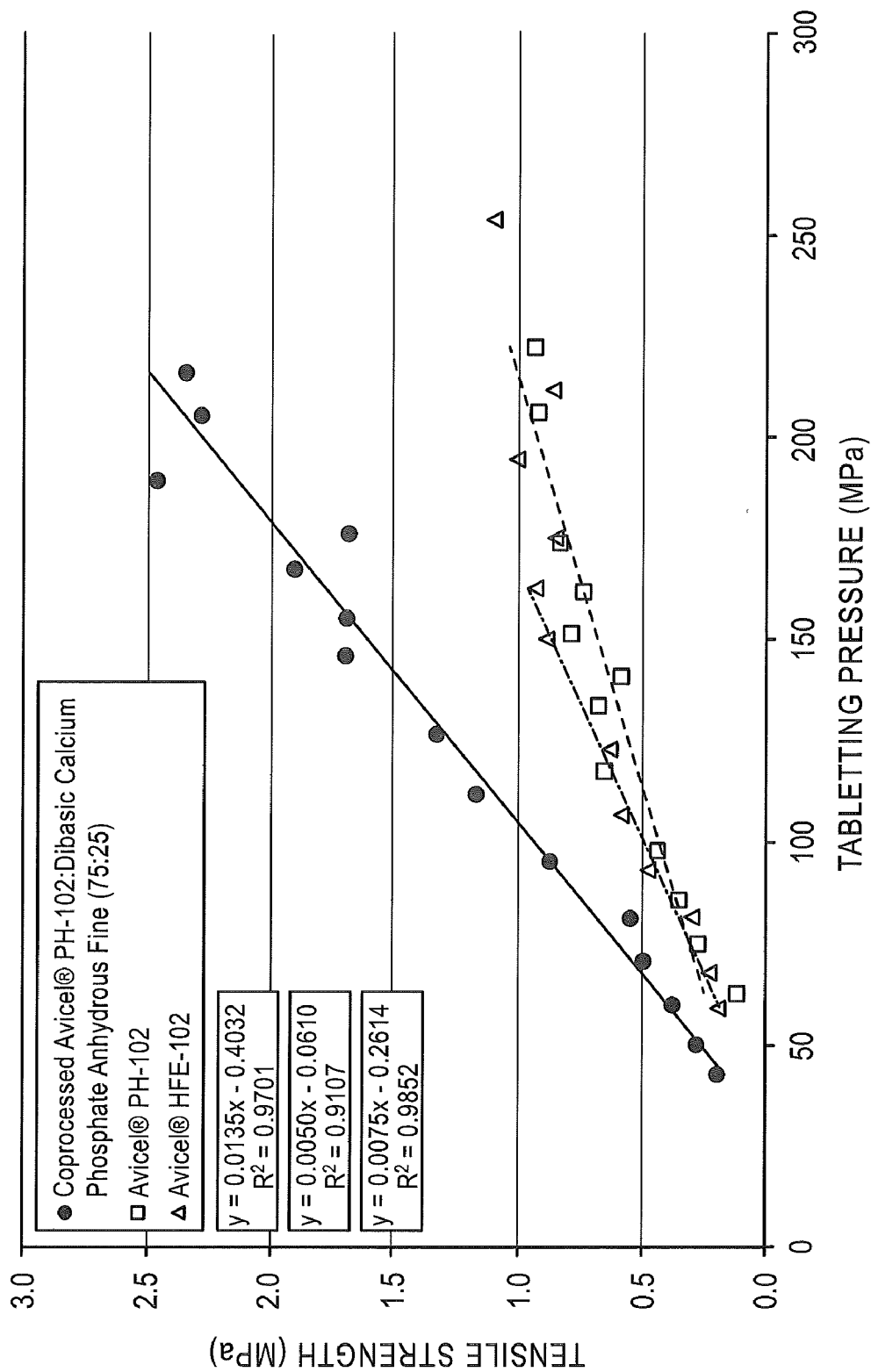
Figure 20:
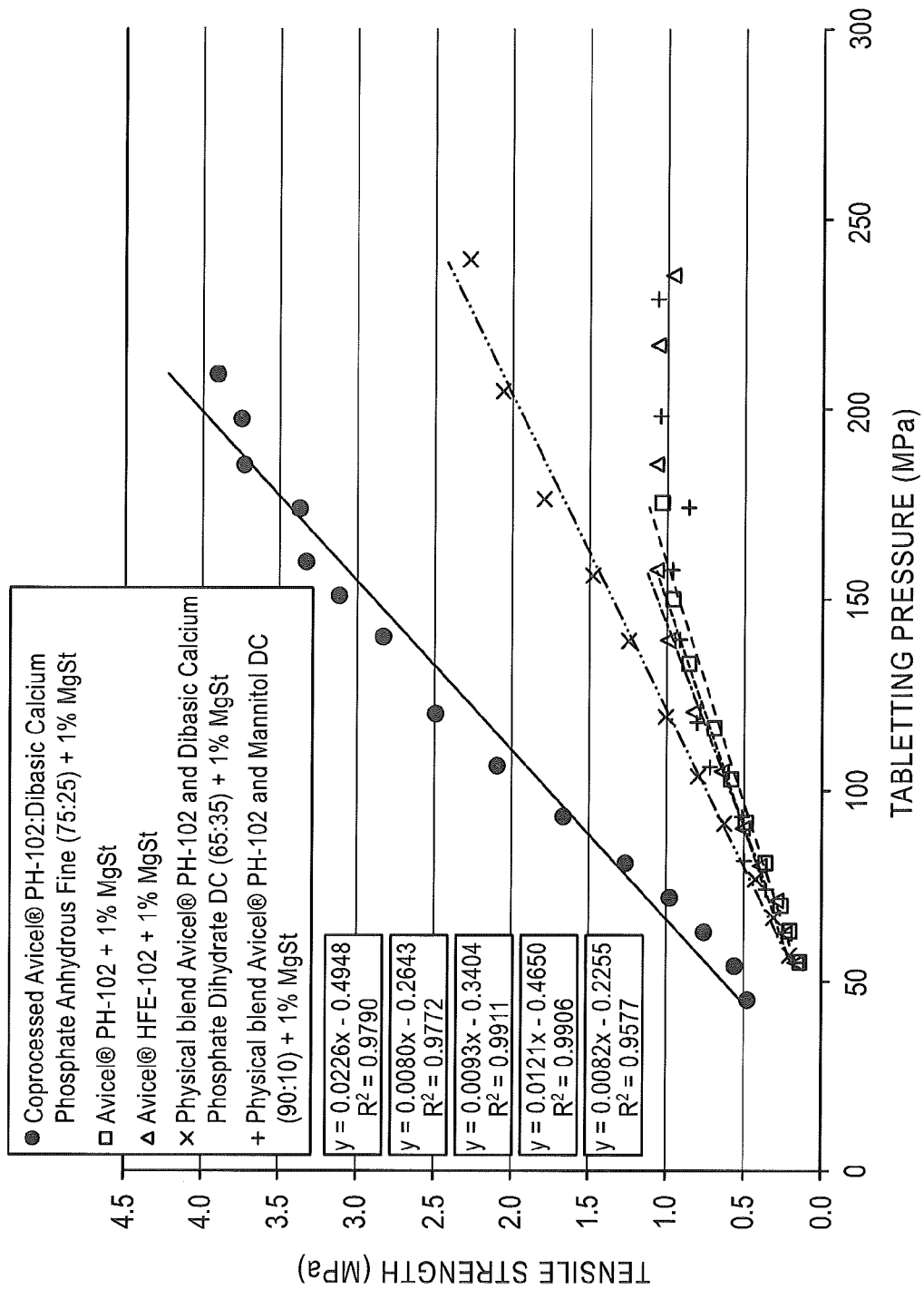

Recompactibility was assessed by tabletting granules from ribbons formed by roller compaction (30 bars) of granulate formulations of coprocessed MCC:DCP particulate product (75:25), commercially-available microcrystalline cellulose products AVICEL® PH-102 and AVICEL® HFE-102, and physical blends of AVICEL® PH-102 with dibasic calcium phosphate or mannitol, respectively. Tabletting data for compacted granules from the Vitamin C granulate formulation (69.5% of the excipient, 30.0% Vitamin C, and 0.5% magnesium stearate) are presented in FIG. 19. Tabletting data for the compacted granules from the placebo granulate formulation (99% excipient and 1% magnesium stearate) are presented in FIG. 20. The MCC:DCP particulate product showed superior recompactibility compared to both commercial excipients when tested in either the 30% Vitamin C or the placebo formulation.

Example 12

Friability and disintegration were tested for Vitamin C tablets containing the MCC:DCP particulate products in comparison with microcrystalline cellulose or physical blends of commercial excipients.

Tablets were prepared from 30% Vitamin C granules (produced by grinding ribbons formed by roller-compaction of granulate formulations of varying excipients at 30 bars) using a Manesty D4 rotary press at 30 rpm using 12 millimeter round normal concave toolings. Friability of the tablets was determined as the % of weight loss by rotating 20 tablets in a Pharma Test PTF1 friability tester for four minutes at 25 rotations per minute (a total of 100 rotations). Tablets were compressed on the Manesty D4 rotary press at 15 kN compression force. The results obtained are shown in Table 9.

TABLE 9

Friability of Vitamin C Tablets

| Excipient in Roller-compacted Vitamin C Granules | Friability, % |
|---|---|
| Coprocessed MCC:DCP participate produce (75:25) | 0.16 |
| AVICEL® PH-101 | 0.31 |
| Physical blend of AVICEL® PH-101 and Dicalcium Phosphate Anhydrous DC (75:25) | 0.32 |
| Physical blend of AVICEL® PH-101 and Dicalcium Phosphate Anhydrous DC (65:35) | 0.56 |
| Physical blend of AVICEL® PH-101 and Lactose Anhydrous DC (50:50) | 0.32 |

Disintegration data are reported in Table 10 for tablets prepared from the Vitamin C granules by varying tabletting force to obtain similar hardness. Disintegration time was determined using the Pharma Test PTZ2 disintegration tester. The disintegration time of tablets prepared using the coprocessed MCC:DCP particulate product (75:25) is shorter than the disintegration time of tablets prepared using either AVICEL® PH-101 or physical blends.

TABLE 10

Disintegration Time for Vitamin C Tablets

| Excipient in Roller-compacted Granules | Tablet Hardness, N | Disintegration time, seconds |
|---|---|---|
| Coprocessed MCC:DCP particulate product (75:25) | 119 | 24 |
| AVICEL® PH-101 | 124 | 33 |
| Physical blend of AVICEL® PH-101 and Dibasic calcium Phosphate Anhydrous DC (75:25) | 123 | 35 |
| Physical blend of AVICEL® PH-101 and Dicalcium Phosphate Anhydrous DC (65:35) | 124 | 40 |
| Physical blend of AVICEL® PH-101 and Lactose Anhydrous DC (50:50) | 122 | 340 |

What is claimed is:

1. A coprocessed composition useful as a pharmaceutical excipient comprising particles of at least one calcium phosphate and particles of microcrystalline cellulose, wherein the microcrystalline cellulose and the at least one calcium phosphate are present (i) in a weight ratio of from about 85:15 to about 55:45 microcrystalline cellulose:calcium phosphate and (ii) in an amount of at least 70% by weight of the coprocessed composition.

2. The coprocessed composition of claim 1, wherein at least a portion of the particles of the at least one calcium phosphate are embedded within pores of the microcrystalline cellulose.

3. The coprocessed composition of claim 1, wherein the composition is in the form of dried particulate agglomerates.

4. The coprocessed composition of claim 3, wherein the agglomerates are obtained by forming a well-dispersed aqueous slurry of microcrystalline cellulose and at least one particulate calcium phosphate and drying the aqueous slurry.

5. The coprocessed composition of claim 1, wherein said at least one calcium phosphate includes dibasic calcium phosphate.

6. The coprocessed composition of claim 1, wherein microcrystalline cellulose and the at least one calcium phosphate are present in a weight ratio of from about 80:20 to about 60:40 microcrystalline cellulose:calcium phosphate.

7. The coprocessed composition of claim 1, wherein the at least one calcium phosphate has a median particle size of less than about 50 μm.

8. The coprocessed composition of claim 1, wherein the at least one calcium phosphate has a median particle size of less than about 20 μm.

9. The coprocessed composition of claim 1, wherein the calcium phosphate includes at least one of dibasic calcium phosphate dihydrate or anhydrous dibasic calcium phosphate.

10. The coprocessed composition of claim 3, wherein the microcrystalline cellulose has a median particle size of about 20 μm to about 250 μm.

11. A process for preparing a composition useful as a pharmaceutical excipient, comprising:
   a) forming a well-dispersed aqueous slurry of microcrystalline cellulose and at least one calcium phosphate, wherein the microcrystalline cellulose and the at least one calcium phosphate are present (i) in a weight ratio of from about 85:15 to about 55:45 microcrystalline cellulose:calcium phosphate and (ii) in an amount of at least 70% by weight of the coprocessed composition; and
   b) drying the aqueous slurry by removing water therefrom to yield a particulate product.

12. The process of claim 11, wherein drying is accomplished by spray drying.

13. The process of claim 11, wherein the aqueous slurry contains 10 to 30 weight percent solids.

14. A granulate or tablet formulation comprising the coprocessed composition of claim 1 and at least one active.

15. The granulate or tablet formulation of claim 14, additionally comprising at least one lubricant.

16. The granulate or tablet formulation of claim 14, additionally comprising at least one disintegrant.

17. A method comprising the steps of:
   a) applying pressure to a granulate formulation to form a compact, wherein the granulate formulation comprises the coprocessed composition of claim 1 and at least one active; and
   b) milling the compact to form a granulate.

18. The method of claim 17, comprising an additional step of:
   c) recompacting the granulate to form a solid dosage form.

19. A solid dosage form comprising the coprocessed composition of claim 1 and at least one active in the form of a compacted tablet.

20. The coprocessed composition of claim 1 wherein said composition consists of said microcrystalline cellulose and calcium phosphate.

* * * * *